(12) United States Patent
Provins et al.

(10) Patent No.: US 8,957,218 B2
(45) Date of Patent: Feb. 17, 2015

(54) 2-OXO-1-IMIDAZOLIDINYL IMIDAZOTHIADIAZOLE DERIVATIVES

(75) Inventors: Laurent Provins, Brussels (BE); Yannick Quesnel, Brussels (BE)

(73) Assignee: UCB Pharma S.A., Brussels (BE)

( * ) Notice: Subject to any disclaimer, the term of this patent is extended or adjusted under 35 U.S.C. 154(b) by 0 days.

(21) Appl. No.: 14/112,663

(22) PCT Filed: Apr. 17, 2012

(86) PCT No.: PCT/EP2012/001658
§ 371 (c)(1),
(2), (4) Date: Jan. 23, 2014

(87) PCT Pub. No.: WO2012/143117
PCT Pub. Date: Oct. 26, 2012

(65) Prior Publication Data
US 2014/0148489 A1    May 29, 2014

Related U.S. Application Data

(60) Provisional application No. 61/480,134, filed on Apr. 28, 2011.

(30) Foreign Application Priority Data

Apr. 18, 2011    (EP) .................... 11162853

(51) Int. Cl.
C07D 417/14    (2006.01)
A61K 31/433    (2006.01)
C07D 513/04    (2006.01)

(52) U.S. Cl.
CPC ............ *C07D 513/04* (2013.01); *A61K 31/433* (2013.01)
USPC .......................................... 548/126; 514/361

(58) Field of Classification Search
None
See application file for complete search history.

(56) References Cited

FOREIGN PATENT DOCUMENTS

WO    2006/128692 A2    12/2006
WO    2008/132142 A2    11/2008

*Primary Examiner* — Nyeemah A Grazier
(74) *Attorney, Agent, or Firm* — McDonnell Boehnen Hulbert & Berghoff LLP

(57) ABSTRACT

The present invention relates to 2-oxo-1-imidazolidinyl imidazothiadiazole derivatives, processes for preparing them, pharmaceutical compositions containing them and their use as pharmaceuticals.

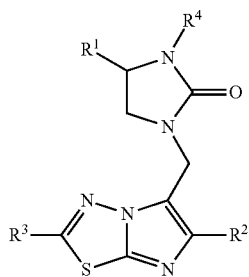

(I)

10 Claims, No Drawings

2-OXO-1-IMIDAZOLIDINYL IMIDAZOTHIADIAZOLE DERIVATIVES

This application is a U.S. national phase of International Application No. PCT/EP2012/001658 filed Apr. 17, 2012, which claims the benefit of priority of European Patent Application No. 11162853.3 filed Apr. 18, 2011 and U.S. Provisional Application No. 61/480,134 filed Apr. 28, 2011, the disclosures of which are incorporated herein by reference in their entirety.

The present invention relates to 2-oxo-1-imidazolidinyl imidazothiadiazole derivatives, processes for preparing them, pharmaceutical compositions containing them and their use as pharmaceuticals.

European Patent No. 0 162 036 B1 discloses compound (S)-α-ethyl-2-oxo-1-pyrrolidine acetamide, which is known under the International Nonproprietary Name (INN) levetiracetam.

Levetiracetam, a levorotary compound, is disclosed as a protective agent for the treatment and prevention of hypoxic and ischemic type aggressions of the central nervous system. This compound is also effective in the treatment of epilepsy (seizure control), a therapeutic indication for which it has been demonstrated that its dextrorotatory enantiomer (R)-α-ethyl-2-oxo-1-pyrrolidine acetamide, also known from European Patent No. 0 165 919 B1, completely lacks activity (Gower A. J. et al., Eur. J. Pharmacol. (1992), 222, 193-203).

A persistent problem in seizure control arises with those patients who do not at all or only insufficiently respond to currently available treatments. Those patients are viewed as being refractory to treatment and represent a considerable challenge for the medical community. It is estimated that about 30% of epilepsy patients are to be classified as being refractory. Hence, there is a need to develop new medications that specifically target this population of patients.

Belavin I. Yu. et al. (Khimiko-Farmatsevticheskii Zhurnal (1992), 26 (9-10), 74-76) discloses 1-[1-(1H-benzimidazol-1-yl)ethyl]-2-pyrrolidinone and its anticonvulsant activity.

WO 01/62726 discloses pyrrolidinone compounds having the following formula:

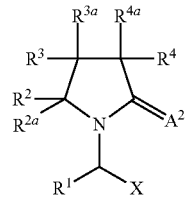

WO 2005/054188 discloses imidazole derivatives having the formula A:

(A)

The imidazole or benzimidazole is attached by a nitrogen to the methylene linker of the pyrrolidinone.

WO 2006/128693 discloses pyrrolidinone compounds of the following formula B:

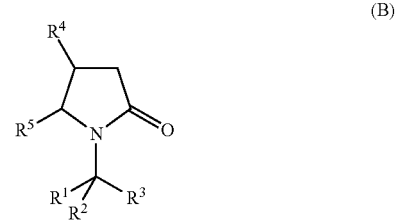

(B)

wherein $R^1$ is hydrogen, substituted or unsubstituted $C_{1-12}$ alkyl, substituted or unsubstituted aryl or substituted or unsubstituted 3-8 membered heterocycle.

$R^2$ is hydrogen. Alternatively, $R^1$ and $R^2$ may be linked together in such a way to form a $C_{3-6}$ cycloalkyl.

$R^3$ is either (a) a substituted or unsubstituted heterocycle linked to the rest of the molecule via one of its C atoms, said heterocycle being selected from the group consisting of:
1H-benzimidazol-6-yl;
1H-benzimidazol-7-yl;
imidazo[1,2-a]pyridin-3-yl;
imidazo[1,2-a]pyrimidin-3-yl;
imidazo[1,2-b][1,2,4]triazin-7-yl;
imidazo[1,2-b]pyridazin-3-yl;
5,6,7,8-tetrahydroimidazo[1,2-b]pyridazin-3-yl;
imidazo[2,1-b][1,3,4]thiadiazol-5-yl;
imidazo[2,1-b][1,3]thiazol-5-yl;
3H-imidazo[4,5-b]pyridin-7-yl;
1H-imidazol-4-yl;
1H-imidazol-5-yl;
1H-indol-2-yl;
1H-indol-3-yl;
1H-indol-4-yl;
1H-indol-7-yl;
isoxazol-4-yl;
1H-pyrazol-4-yl;
1H-pyrazol-5-yl;
1H-pyrazolo[1,5-a]pyrimidin-3-yl;
1H-pyrazolo[3,4-b]pyridin-3-yl;
pyridazin-4-yl;
pyridin-2-yl;
pyridin-3-yl;
pyridin-4-yl;
1H-pyrrolo[2,3-b]pyridin-3-yl;
1H-pyrrolo[2,3-b]pyridin-4-yl;
1H-pyrrolo[2,3-b]pyridin-5-yl;
1H-pyrrolo[2,3-c]pyridin-2-yl;
1H-pyrrolo[2,3-c]pyridin-3-yl;
1H-pyrrolo[3,2-b]pyridin-3-yl;
1H-pyrrolo[3,2-c]pyridin-2-yl;
1H-pyrrolo[3,2-c]pyridin-3-yl;
1,3,4-thiadiazol-2-yl;
1,3-thiazol-5-yl;
[1,2,4]triazolo[4,3-b]pyridazin-7-yl;
[1,2,4]triazolo[4,3-b]pyridazin-8-yl;
indolizin-3-yl;

or alternatively $R^3$ is
(b) a substituted or unsubstituted heterocycle linked to the rest of the molecule via one of its N atoms, said heterocycle being selected from the group consisting of:
1H-1,2,3-benzotriazol-1-yl;
1H-imidazo[4,5-b]pyridin-1-yl;
3H-imidazo[4,5-b]pyridin-3-yl;
7H-imidazo[4,5-c]pyridazin-7-yl;
1H-indol-1-yl;
2,3-dihydro-1H-indol-1-yl;
9H-purin-9-yl;
1H-pyrazolo[3,4-b]pyridin-1-yl;
2H-pyrazolo[3,4-b]pyridin-2-yl;
1H-pyrrolo[2,3-b]pyridin-1-yl;
1H-pyrrolo[3,2-b]pyridin-1-yl;
3,4-dihydroquinolin-1(2H)-yl;
8H-isothiazolo[5,4-b]indol-8-yl;
1H-1,2,4-triazol-1-yl;
1H-pyrrol-1-yl;
2-chloro-1H-benzimidazol-1-yl.

$R^4$ in formula (I) is selected from the group comprising or consisting of hydrogen; $C_{1-12}$ alkyl optionally substituted by halogen, $C_{1-4}$ alkoxy, $C_{1-4}$ alkylthio, azido, nitrooxy or an aryl; $C_{2-12}$ alkenyl optionally substituted by halogen; $C_{2-12}$ alkynyl optionally substituted by halogen; azido; alkoxycarbonylamino; arylsulfonyloxy; a substituted or unsubstituted aryl; or a 3-8 membered substituted or unsubstituted heterocycle.

The compounds of WO 2006/128693 are said to be useful in the treatment of epilepsy, epileptogenesis, seizure disorders, convulsions, Parkinson's disease, dyskinesia induced by dopamine replacement therapy, tardive dyskinesia induced by administration of neuroleptic drugs, Huntington Chorea, and other neurological disorders including bipolar disorders, mania, depression, anxiety, attention deficit hyperactivity disorder (ADHD), migraine, trigeminal and other neuralgia, chronic pain, neuropathic pain, cerebral ischemia, cardiac arrhythmia, myotonia, cocaine abuse, stroke, myoclonus, tremor, essential tremor, simple or complex tics, Tourette syndrome, restless legs syndrome and other movement disorders, neonatal cerebral haemorrhage, amyotrophic lateral sclerosis, spasticity and degenerative diseases, bronchial asthma, asthmatic status and allergic bronchitis, asthmatic syndrome, bronchial hyperreactivity and bronchospastic syndromes as well as allergic and vasomotor rhinitis and rhinoconjunctivitis.

Further anti-epileptic compounds of formula C are disclosed in WO 2008/132139:

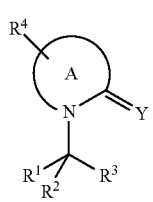
(C)

wherein
Y is O or S;
$R^1$ is hydrogen or $C_{1-6}$ alkyl;
$R^2$ is hydrogen;
$R^3$ is —$CONR^5R^6$, —$COR^7$, an imidazolyl, an imidazopyridinyl, an imidazopyridazinyl;
$R^5$, $R^6$ are the same or different and are independently selected from hydrogen and $C_{1-6}$ alkyl;
$R^7$ is $C_{1-6}$ alkyl;
A is a monocyclic or bicyclic heterocyclic moiety selected from the group consisting of imidazolidin-1-yl, 1,3-oxazolidin-3-yl, 2,5-dihydro-1H-pyrrol-1-yl, 1,3-thiazol-3(2H)-yl, 1,3-thiazolidin-3-yl, piperidin-1-yl, azepan-1-yl, 5,6-dihydro-4H-thieno[3,2-b]pyrrol-4-yl, hexahydro-4H-thieno[3,2-b]pyrrol-4-yl, 2,3-dihydro-1H-thieno[3,4-b]pyrrol-1-yl, 1,3-benzothiazol-3(2H)-yl, 1,3-benzoxazol-3(2H)-yl, pyrazolo[1,5-a]pyridin-1(2H)-yl, 3,4-dihydroisoquinolin-2(1H)-yl, 3,4-dihydroquinolin-1(2H)-yl, 1,3,4,5-tetrahydro-2H-2-benzazepin-2-yl, 1,2,4,5-tetrahydro-3H-3-benzazepin-3-yl;

In a specific embodiment of WO 2008/132139 the A=Y moiety in formula (C) could be:

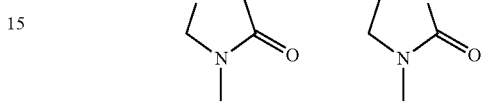

wherein X is O or S.

SUMMARY OF THE INVENTION

The invention provides new 2-oxo-1-imidazolidinyl imidazothiadiazole derivatives having the formula (I), their geometrical isomers, enantiomers, diastereoisomers and mixtures, or a pharmaceutically acceptable salt thereof,

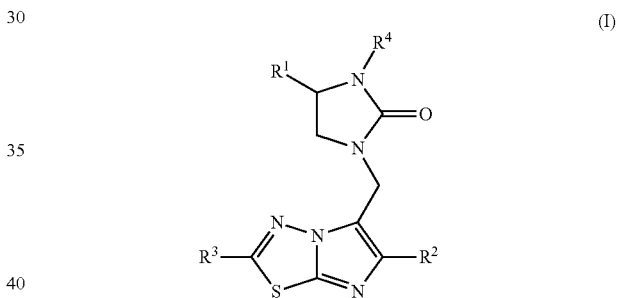
(I)

Further aspects of the invention will become apparent from the detailed description.

DETAILED DESCRIPTION OF THE INVENTION

The present invention relates to 2-oxo-1-imidazolidinyl imidazothiadiazole derivatives according to formula (I),

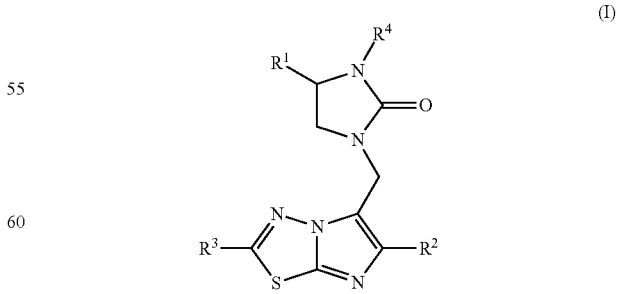
(I)

wherein
$R^1$ is a $C_{1-4}$ alkyl or a $C_{2-4}$ alkenyl optionally substituted by one or more (i.e. 1, 2 or 3) halogen substituents.

$R^2$ is either a halogen (chlorine, bromine, iodine) or a $C_{1-4}$ alkyl containing at least one (i.e. 1, 2 or 3) halogen substituent.

$R^3$ is a $C_{1-4}$ alkyl (e.g. a methyl or an ethyl moiety) containing at least one hydroxy (OH) or an alkoxy (e.g. methoxy or ethoxy or propoxy) substituent.

$R^4$ is either hydrogen or a methyl group.

The present invention relates in particular to 2-oxo-1-imidazolidinyl imidazothiadiazole derivatives according to formula (I-A),

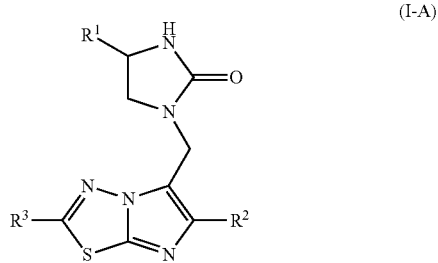

(I-A)

wherein
$R^1$ is a $C_{1-4}$ alkyl or a $C_{2-4}$ alkenyl optionally substituted by one or more (i.e. 1, 2 or 3) halogen substituents.

$R^2$ is either a halogen (chlorine, bromine, iodine) or a $C_{1-4}$ alkyl containing at least one (i.e. 1, 2 or 3) halogen substituent.

$R^3$ is a $C_{1-4}$ alkyl (e.g. a methyl or an ethyl moiety) containing at least one hydroxy (OH) or an alkoxy (e.g. methoxy or ethoxy or propoxy) substituent.

The present invention relates also to 2-oxo-1-imidazolidinyl imidazothiadiazole derivatives according to formula (I-B),

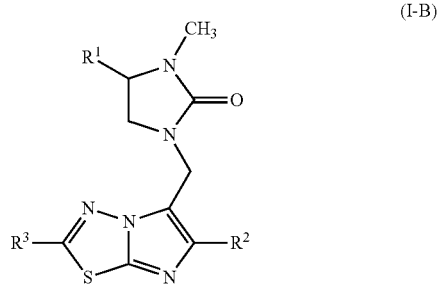

(I-B)

wherein
$R^1$ is a $C_{1-4}$ alkyl or a $C_{2-4}$ alkenyl optionally substituted by one or more (i.e. 1, 2 or 3) halogen substituents.

$R^2$ is either a halogen (chlorine, bromine, iodine) or a $C_{1-4}$ alkyl containing at least one (i.e. 1, 2 or 3) halogen substituent.

$R^3$ is a $C_{1-4}$ alkyl (e.g. a methyl or an ethyl moiety) containing at least one hydroxy (OH) or an alkoxy (e.g. methoxy or ethoxy or propoxy) substituent.

Also comprised are tautomers, geometrical isomers, enantiomers, diastereomers and mixtures, or a pharmaceutically acceptable salt of compounds of formula (I) as well as any deuterated variant.

In a specific embodiment, $R^1$ is a $C_{1-4}$ alkyl optionally substituted by one or more (i.e. 1, 2 or 3) halogen substituents.

In another specific embodiment, $R^1$ is an i-butyl, a n-propyl, a 2,2-difluoropropyl, a 2-chloro-2,2-difluoroethyl, a 2,2-difluoroethyl, a 2,2,2-trifluoroethyl, a 3,3,3-trifluoropropyl, a 2-fluoroethyl or a 2,2-difluoroethenyl moiety, preferably an i-butyl, a n-propyl, a 2-chloro-2,2-difluoroethyl, a 2,2,2-trifluoroethyl, a 3,3,3-trifluoropropyl or a 2,2-difluoroethenyl group. More preferably $R^1$ is an i-butyl, a n-propyl, a 2-chloro-2,2-difluoroethyl, a 2,2,2-trifluoroethyl or a 3,3,3-trifluoropropyl group.

In a further specific embodiment, $R^2$ is a chloro, a difluoromethyl or a trifluoromethyl moiety, preferably a chloro or a trifluoromethyl moiety.

In a further specific embodiment, $R^3$ is either a hydroxymethyl, a methoxymethyl, a [($^2H_3$)methyloxy]methyl, a methoxy($^2H_2$)methyl, a (2,2,2-trifluoroethoxy)methyl or a 2-methoxyethyl moiety, preferably a methoxymethyl moiety.

In a further specific embodiment, compounds of formula (I), (I-A) and (I-B) are those wherein:
$R^1$ is a i-butyl, n-propyl, a 2-chloro-2,2-difluoroethyl, 2,2,2-trifluoroethyl, a 3,3,3-trifluoropropyl or a 2,2-difluoroethenyl moiety; preferably i-butyl, n-propyl, a 2-chloro-2,2-difluoroethyl, a 2,2,2-trifluoroethyl or a 3,3,3-trifluoropropyl moiety;
$R^2$ is a chloro or a trifluoromethyl moiety;
$R^3$ is a methoxymethyl moiety;
$R^4$ is hydrogen or methyl.

Specific compounds of the present invention are those selected from the group consisting of:

1-{[2-(methoxymethyl)-6-(trifluoromethyl)imidazo[2,1-b][1,3,4]thiadiazol-5-yl]methyl}-4-(2-methylpropyl)imidazolidin-2-one;

(−)-1-{[2-(methoxymethyl)-6-(trifluoromethyl)imidazo[2,1-b][1,3,4]thiadiazol-5-yl]methyl}-4-(2-methylpropyl)imidazolidin-2-one;

(+)-1-{[2-(methoxymethyl)-6-(trifluoromethyl)imidazo[2,1-b][1,3,4]thiadiazol-5-yl]methyl}-4-(2-methylpropyl)imidazolidin-2-one;

1-{[2-(methoxymethyl)-6-(trifluoromethyl)imidazo[2,1-b][1,3,4]thiadiazol-5-yl]methyl}-4-propylimidazolidin-2-one;

(−)-1-{[2-(methoxymethyl)-6-(trifluoromethyl)imidazo[2,1-b][1,3,4]thiadiazol-5-yl]methyl}-4-propylimidazolidin-2-one;

(+)-1-{[2-(methoxymethyl)-6-(trifluoromethyl)imidazo[2,1-b][1,3,4]thiadiazol-5-yl]methyl}-4-propylimidazolidin-2-one;

1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one;

(−)-1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one;

(+)-1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one;

1-{[6-chloro-2-(methoxymethyl)imidazo[2,1-b][1,3,4]thiadiazol-5-yl]methyl}-4-(3,3,3-trifluoropropyl)imidazolidin-2-one;

(−)-1-{[6-chloro-2-(methoxymethyl)imidazo[2,1-b][1,3,4]thiadiazol-5-yl]methyl}-4-(3,3,3-trifluoropropyl)imidazolidin-2-one;

(+)-1-{[6-chloro-2-(methoxymethyl)imidazo[2,1-b][1,3,4]thiadiazol-5-yl]methyl}-4-(3,3,3-trifluoropropyl)imidazolidin-2-one;

1-{[2-(methoxymethyl)-6-(trifluoromethyl) imidazo[2,1-b][1,3,4]thiadiazol-5-yl]methyl}-4-(2,2,2-trifluoroethyl)imidazolidin-2-one;

(+)-1-{[2-(methoxymethyl)-6-(trifluoromethyl)imidazo[2,1-b][1,3,4]thiadiazol-5-yl]methyl}-4-(2,2,2-trifluoroethyl)imidazolidin-2-one;
(−)-1-{[2-(methoxymethyl)-6-(trifluoromethyl)imidazo[2,1-b][1,3,4]thiadiazol-5-yl]methyl}-4-(2,2,2-trifluoroethyl)imidazolidin-2-one;
4-(2-chloro-2,2-difluoroethyl)-1-{[2-(methoxymethyl)-6-(trifluoromethyl) imidazo[2,1-b][1,3,4]thiadiazol-5-yl]methyl}imidazolidin-2-one;
(+)-4-(2-chloro-2,2-difluoroethyl)-1-{[2-(methoxymethyl)-6-(trifluoromethyl)imidazo[2,1-b][1,3,4]thiadiazol-5-yl]methyl}imidazolidin-2-one;
(−)-4-(2-chloro-2,2-difluoroethyl)-1-{[2-(methoxymethyl)-6-(trifluoromethyl) imidazo[2,1-b][1,3,4]thiadiazol-5-yl]methyl}imidazolidin-2-one;
4-(2,2-difluoroethenyl)-1-{[2-(methoxymethyl)-6-(trifluoromethyl)imidazo[2,1-b][1,3,4]thiadiazol-5-yl]methyl}imidazolidin-2-one;
4-(2-chloro-2,2-difluoroethyl)-1-{[2-(hydroxymethyl)-6-(trifluoromethyl)imidazo[2,1-b][1,3,4]thiadiazol-5-yl]methyl}imidazolidin-2-one;
1-{[2-(hydroxymethyl)-6-(trifluoromethyl)imidazo[2,1-b][1,3,4]thiadiazol-5-yl]methyl}-4-(2,2,2-trifluoroethyl) imidazolidin-2-one;
(+)-4-(2-chloro-2,2-difluoroethyl)-1-{[2-(methoxymethyl)-6-(trifluoromethyl)imidazo[2,1-b][1,3,4]thiadiazol-5-yl]methyl}-3-methylimidazolidin-2-one;
(−)-4-(2-chloro-2,2-difluoroethyl)-1-{[2-(methoxymethyl)-6-(trifluoromethyl)imidazo[2,1-b][1,3,4]thiadiazol-5-yl]methyl}-3-methylimidazolidin-2-one.

The following paragraphs provide definitions of the various chemical moieties that make up the compounds according to the invention and are intended to apply uniformly throughout the specification and claims unless an otherwise expressly set out definition provides a broader definition.

"$C_{1-4}$ alkyl" refers to alkyl groups having 1 to 4 carbon atoms. This term is exemplified by groups such as methyl, ethyl, n-propyl, isopropyl, n-butyl, isobutyl, tert-butyl. "$C_{1-4}$ alkyl" groups may be substituted by one or more substituents selected from halogen, hydroxy or alkoxy.

"$C_{2-4}$ alkenyl" refers to alkenyl groups preferably having from 2 to 4 carbon atoms and having at least 1 or 2 sites of alkenyl unsaturation. Preferable alkenyl groups include ethenyl (vinyl, —CH=CH$_2$), n-2-propenyl (allyl, —CH$_2$CH=CH$_2$) and the like. "$C_{2-4}$ alkenyl" groups may be substituted by one or more halogen atoms.

Any moiety "H" in formula (I) may be the isotope hydrogen, deuterium or tritium.

"Hydroxy" represents a group of formula —OH.

"Alkoxy" refers to the group —O—R where R includes "$C_{1-4}$ alkyl".

"Halogen" refers to fluoro, chloro, bromo and iodo atoms, preferably fluoro and chloro.

The "pharmaceutically acceptable salts" according to the invention include therapeutically active, non-toxic acid or base salt forms which the compounds of formula (I) are able to form.

The acid addition salt form of a compound of formula (I) that occurs in its free form as a base can be obtained by treating the free base with an appropriate acid such as an inorganic acid, for example, a hydrohalic such as hydrochloric or hydrobromic, sulfuric, nitric, phosphoric and the like; or an organic acid, such as, for example, acetic, trifluoroacetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like.

The compounds of formula (I) containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Conversely said salt forms can be converted into the free forms by treatment with an appropriate base or acid.

Compounds of the formula (I) and their salts can be in the form of a solvate, which is included within the scope of the present invention. Such solvates include for example hydrates, alcoholates and the like.

Compounds of formula (I) and/or their intermediates may have at least one stereogenic center in their structure. This stereogenic center may be present in a R or a S configuration, said R and S notation is used in correspondence with the rules described in Pure Appl. Chem., 45 (1976) 11-30. The invention thus also relates to all stereoisomeric forms such as enantiomeric and diastereoisomeric forms of the compounds of formula (I) or mixtures thereof (including all possible mixtures of stereoisomers). With respect to the present invention reference to a compound or compounds is intended to encompass that compound in each of its possible isomeric forms and mixtures thereof, unless the particular isomeric form is referred to specifically. The expression "enantiomerically pure" as used herein refers to compounds which have enantiomeric excess (ee) greater than 95%.

Compounds according to the present invention may exist in different polymorphic forms. Although not explicitly indicated in the above formula, such forms are intended to be included within the scope of the present invention.

The compounds of formula (I) according to the invention can be prepared analogously to conventional methods as understood by the person skilled in the art of synthetic organic chemistry.

According to one embodiment, compounds having the general formula (I) wherein $R^4$ is hydrogen may be prepared by reaction of a compound of formula II with an urea of formula III according to the equation:

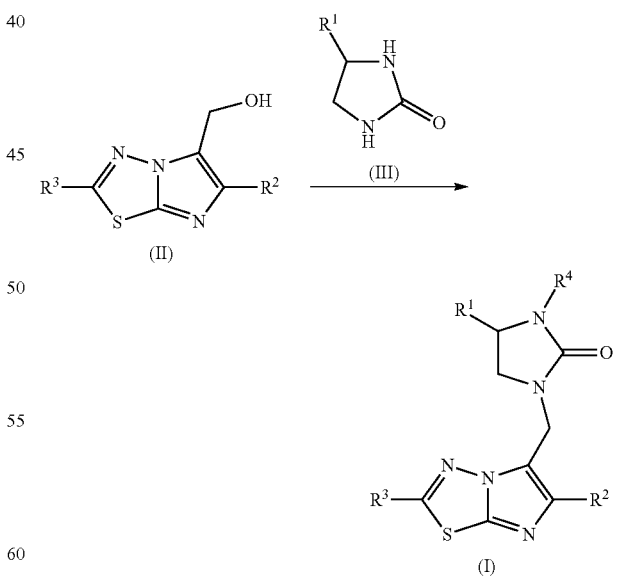

wherein $R^1$, $R^2$ and $R^3$ have the same definitions as defined above for compounds of formula I and $R^4$ is hydrogen.

This reaction may be performed using an acid such as p-toluenesulphonic acid in an aprotic solvent such as toluene at reflux temperature.

Compounds of formula II wherein $R^2$ is a halogen atom may be prepared by reduction of a compound of formula IV according to the equation:

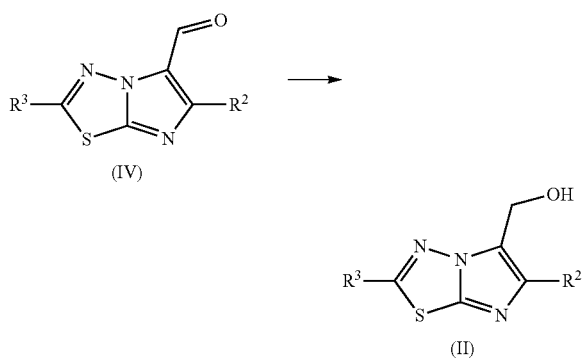

wherein $R^2$ is a halogen atom and $R^3$ has the same definition as defined above for compounds of formula I.

This reaction may be performed using a reducing agent such as, but not limited to, sodium borohydride in a polar solvent such as ethanol at 0° C. or according to any other method known to the person skilled in the art.

Compounds of formula IV may be prepared by formylation of a compound of formula V according to the equation:

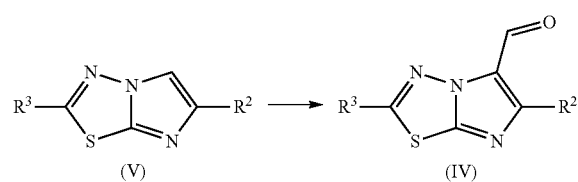

wherein $R^2$ is a halogen atom and $R^3$ has the same definition as defined above for compounds of formula I.

This reaction may be performed using a formylating agent such as dimethylformamide in the presence of phosphorous oxychloride at temperatures ranging from 0° to 60° C., or according to any other method known to the person skilled in the art.

Compounds of formula II wherein $R^2$ is $C_{1-4}$ alkyl may be prepared by formylation of a compound of formula V according to the equation:

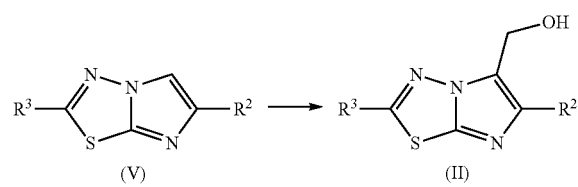

wherein $R^2$ is $C_{1-4}$ alkyl and $R^3$ has the same definition as defined above for compounds of formula I.

This reaction may be performed using a formylating agent such as formaldehyde under acidic conditions in a polar solvent such as sulfolane at 110° C., or according to any other method known to the person skilled in the art.

Compounds of formula V wherein $R^2$ is $C_{1-4}$ alkyl may be synthesized by reaction of a compound of formula VI with a bromo derivative of formula VII according to the equation:

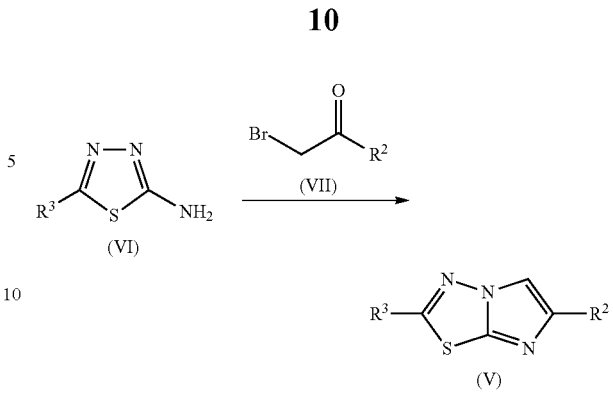

wherein $R^2$ is $C_{1-4}$ alkyl and $R^3$ has the same definition as described above for compounds of formula I.

This reaction can be performed using procedures described in the literature or known to the person skilled in the art.

Compounds of formula V wherein $R^2$ is Cl may be prepared by cyclisation of a compound of formula VIII according to the equation:

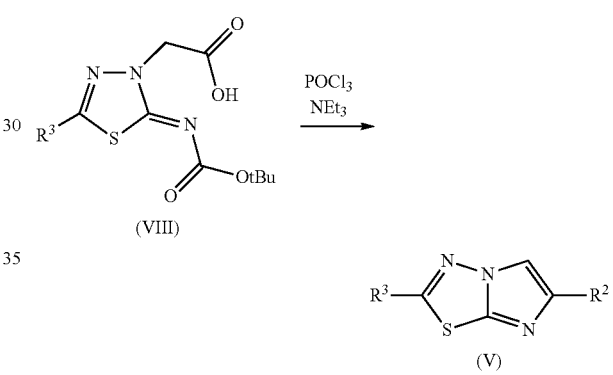

wherein $R^2$ is Cl and $R^3$ has the same definition as described above for compounds of formula I.

This reaction can be performed by treatment of a compound of formula VIII with a halogenating agent such as phosphorus oxychloride with a tertiary amine such as triethylamine in classical organic solvent such as acetonitrile, or according to any other method known by the person skilled in the art.

Compound of formula VIII may be prepared from compound of formula VI, by protection of its amino group by a Boc group, then by reaction of the resulting intermediate with a bromo derivative of formula VII wherein $R^2$ is OH, according to the equation:

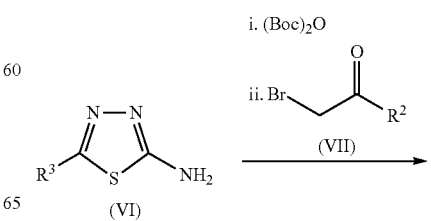

-continued

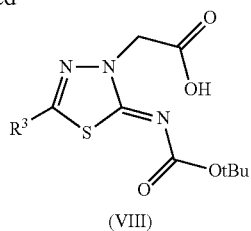

(VIII)

This reaction may be performed using procedures described in the literature or known to the person skilled in the art.

Compounds of formula III may be prepared by deprotection of a compound of formula IX according to the equation:

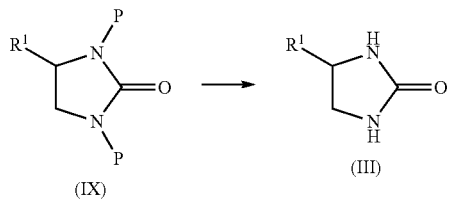

wherein $R^1$ has the same definition as defined above for compounds of formula (I) and P is a protecting group, such as a Boc group.

This reaction may be performed using procedures described in the literature or known to the person skilled in the art.

Compounds of formula IX may be prepared by cyclization of a compound of formula X according to the equation:

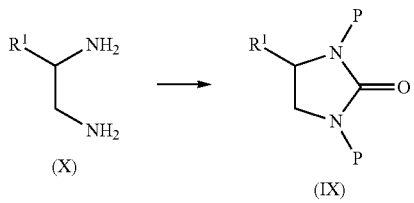

wherein $R^1$ and P have the same definition as defined above.

This reaction may be performed using di-tert-butyl dicarbonate in the presence of a base such as 4-dimethylaminopyridine, in a polar solvent such as acetonitrile at room temperature or using procedures known to the person skilled in the art.

Compounds of formula X may be prepared by reduction of a compound of formula XI according to the equation

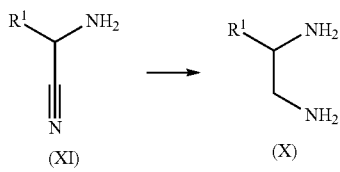

wherein $R^1$ has the same definition as defined above for compounds of formula I.

This reaction may be performed using a reducing agent such as, but not limited to, lithium aluminium hydride in a solvent such as THF at a temperature ranging from 0° C. to 60° C. or by other procedures known to the person skilled in the art.

Compounds of formula XI may be prepared by reaction of an aldehyde of formula XII with cyanides and ammonia according to the equation

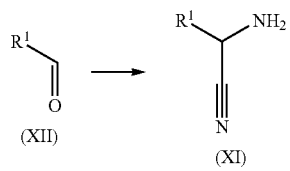

wherein $R^1$ has the same definition as defined above for compounds of formula I.

This reaction may be performed using a cyanide source such as sodium or potassium cyanide, and an ammonia source such as ammonium chloride in acidic conditions in a polar solvent such as methanol at room temperature.

According to another embodiment, compounds having the general formula (I) wherein $R^1$ is 2-chloro-2,2-difluoroethyl and $R^4$ is hydrogen may be prepared by hydrochloration of a compound of formula XIII according to the equation:

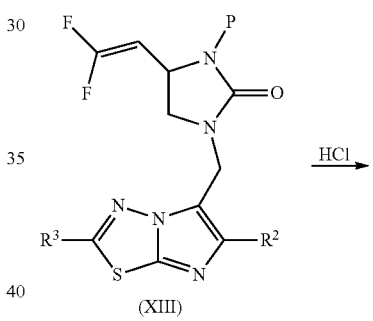

(XIII)

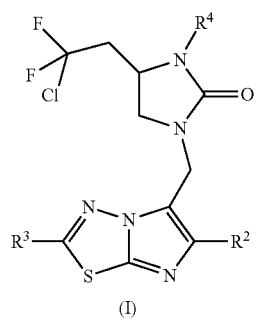

(I)

wherein $R^2$ and $R^3$ have the same definitions as defined above for compounds of formula (I), $R^4$ is hydrogen and P is a protecting group such as an ethylester.

This reaction may be performed using a source of hydrochloric acid such as 37% HCl solution in a polar solvent such as THF at 80° C.

Compounds having the general formula XIII may be prepared by transformation of a compound of formula XIV according to the equation:

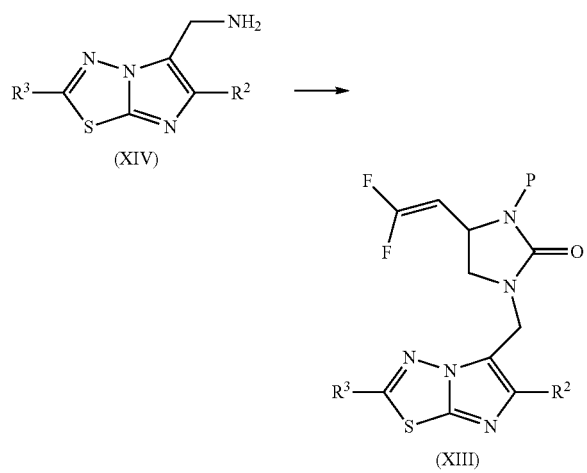

(XIV)

(XIII)

wherein R² and R³ have the same definitions as defined above for compounds of formula I.

This reaction may be performed in a three steps sequence by the addition of 4-bromo-1,1,1-trifluorobut-2-ene to the amine XIV in the presence of a base such as sodium carbonate in a polar solvent such as dimethylformamide at room temperature, followed by the addition of an isocyanate such as ethoxycarbonyl isocyanate at room temperature, followed by the addition of a base such as potassium tert-butoxide at a temperature ranging from 60 to 80° C.

Compounds of formula XIV may be prepared by reduction of a compound of formula XV according to the equation:

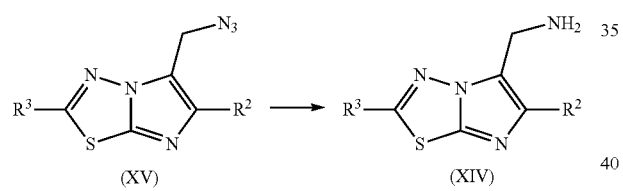

(XV)          (XIV)

wherein R² and R³ have the same definitions as defined above for compounds of formula I.

This reaction may be performed using a reducing agent such as triphenylphosphine in in a THF/water mixture at room temperature or according to any method known to the person skilled in the art.

Compounds of formula XV may be prepared by transformation of a compound of formula II according to the equation:

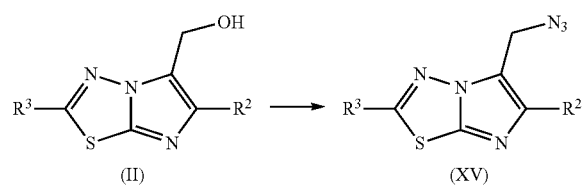

(II)          (XV)

wherein R² and R³ have the same definitions as defined above for compounds of is formula I.

This reaction may be performed in a two-steps sequence by treatment of compounds II with a sulfonyl chloride such as methanesulfonyl chloride in the presence of a base such as N,N-diisopropylethylamine in dichloromethane at 0° C., or according to any other method known to the person skilled in the art, followed by treatment of the intermediate with an azide derivative such as sodium azide in DMF at 0° C. Alternatively, compounds II may be directly treated with diphenylphosphorylazide in the presence of a base such as DBU in THF, or according to any other method known to the person skilled in the art.

Compounds having the general formula (I) wherein R³ is hydroxymethyl and R⁴ is hydrogen may be prepared by hydrochloration of a compound of formula XIII wherein R³ is methoxymethyl and P is a protecting group such as an ethylester, R¹ and R² having the same definitions as defined above for compounds of formula (I).

This reaction may be performed using a source of hydrochloric acid such as 37% HCl solution at high temperature (above 100° C.).

Compounds having the general formula I wherein R⁴ is a methyl moiety may be prepared by N-methylation of the corresponding compound of formula I wherein R⁴ is hydrogen according to the equation:

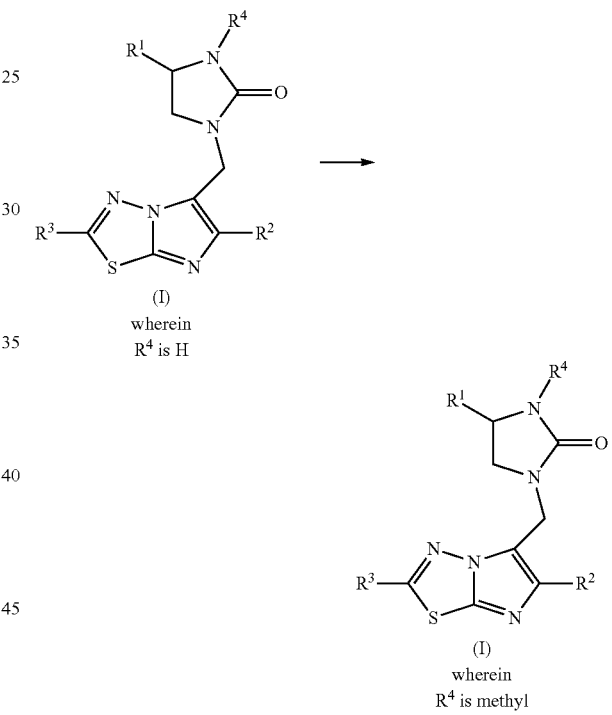

(I)
wherein
R⁴ is H (I)
wherein
R⁴ is methyl wherein R¹, R² and R³ have the same definitions as defined above for compounds of formula (I).

This reaction may be performed using a methylating agent such as methyl iodide in the presence of a base such as sodium hydroxide and an ammonium salt.

In another embodiment, the present invention includes the synthesis of the following intermediates:

[2-(methoxymethyl)-6-(trifluoromethyl)imidazo[2,1-b][1,3,4]thiadiazol-5-yl]methanol;

2-amino-5,5,5-trifluoropentanenitrile;

5,5,5-trifluoropentane-1,2-diamine;

di-tert-butyl 2-oxo-4-(3,3,3-trifluoropropyl)imidazolidine-1,3-dicarboxylate;

di-tert-butyl 2-oxo-4-propylimidazolidine-1,3-dicarboxylate;

di-tert-butyl 4-(2-methylpropyl)-2-oxoimidazolidine-1,3-dicarboxylate;

4-(3,3,3-trifluoropropyl)imidazolidin-2-one;
4-(2-methylpropyl)imidazolidin-2-one;
6-chloro-2-(methoxymethyl)imidazo[2,1-b][1,3,4]thiadiazole-5-carbaldehyde;
[6-chloro-2-(methoxymethyl)imidazo[2,1-b][3,4]thiadiazol-5-yl]methanol;
5-(azidomethyl)-2-(methoxymethyl)-6-(trifluoromethyl)imidazo[2,1-b][1,3,4]thiadiazole;
1-[2-(methoxymethyl)-6-(trifluoromethyl)imidazo[2,1-b][1,3,4]thiadiazol-5-yl]methanamine;
4,4,4-trifluoro-N-{[2-(methoxymethyl)-6-(trifluoromethyl)imidazo[2,1-b][1,3,4]-thiadiazol-5-yl]methyl}but-2-en-1-amine;
ethyl ({[2-(methoxymethyl)-6-(trifluoromethyl)imidazo[2,1-b][1,3,4]thiadiazol-5-yl]-methyl}[(4,4,4-trifluorobut-2-en-1-yl]carbamoyl)carbamate;
ethyl 5-(2,2-difluoroethenyl)-3-{[2-(methoxymethyl)-6-(trifluoromethyl)imidazo-[2,1-b]-[1,3,4]thiadiazol-5-yl]methyl}-2-oxoimidazolidine-1-carboxylate; and
ethyl 3-{[2-(methoxymethyl)-6-(trifluoromethyl)imidazo[2,1-b][1,3,4]thiadiazol-5-yl]methyl}-2-oxo-5-(2,2,2-trifluoroethyl)imidazolidine-1-carboxylate.

The compounds of the present invention are for use as a medicament, in the treatment of epilepsy, epileptogenesis, seizure disorders, convulsions, in particular for refractory seizures.

Seizures can be classified as refractory when a patient fails to achieve seizure freedom for 12 months or more of state of the art treatment with two or more anti-epileptic drugs at maximal tolerated doses. The International League Against Epilepsy (ILAE) has defined drug resistant epilepsy as "failure of adequate trials of two tolerated and appropriately chosen and used AED schedules (whether as monotherapies or in combination) to achieve sustained seizure freedom".

The methods of the invention comprise administration to a mammal (preferably a human) suffering from above mentioned conditions or disorders, of a compound according to the invention in an amount sufficient to alleviate or prevent the disorder or condition.

The compound is conveniently administered in any suitable unit dosage form, including but not limited to one containing 1 to 2000 mg, preferably 1 to 1000 mg, more preferably 1 to 500 mg of active ingredient per unit dosage form.

The term "treatment" as used herein includes curative treatment and prophylactic treatment.

By "curative" is meant efficacy in treating a current symptomatic episode of a disorder or condition.

By "prophylactic" is meant prevention of the occurrence or recurrence of a disorder or condition.

The term "epilepsy" as used herein refers to a chronic neurologic condition characterised by unprovoked, recurrent epileptic seizures. An epileptic seizure is the manifestation of an abnormal and excessive synchronised discharge of a set of cerebral neurons; its clinical manifestations are sudden and transient. The term "epilepsy" as used herein can also refer to a disorder of brain function characterised by the periodic occurrence of seizures. Seizures can be "nonepileptic" when evoked in a normal brain by conditions such as high fever or exposure to toxins or "epileptic" when evoked without evident provocation.

The term "seizure" as used herein refers to a transient alteration of behaviour due to the disordered, synchronous, and rhythmic firing of populations of brain neurones.

A further aspect of the present invention relates to a pharmaceutical composition comprising an effective amount of a compound of formula (I) in combination with a pharmaceutically acceptable diluent or carrier.

Activity in any of the above-mentioned indications can of course be determined by carrying out suitable clinical trials in a manner known to a person skilled in the relevant art for the particular indication and/or in the design of clinical trials in general.

For treating diseases, compounds of formula (I) or their pharmaceutically acceptable salts may be employed at an effective daily dosage and administered in the form of a pharmaceutical composition.

Therefore, another embodiment of the present invention concerns a pharmaceutical composition comprising an effective amount of a compound of formula (I) or a pharmaceutically acceptable salt thereof in combination with a pharmaceutically acceptable diluent or carrier.

To prepare a pharmaceutical composition according to the invention, one or more of the compounds of formula (I) or a pharmaceutically acceptable salt thereof is intimately admixed with a pharmaceutical diluent or carrier according to conventional pharmaceutical compounding techniques known to the skilled practitioner.

Suitable diluents and carriers may take a wide variety of forms depending on the desired route of administration, e.g., oral, rectal, parenteral or intranasal.

Pharmaceutical compositions comprising compounds according to the invention can, for example, be administered orally, parenterally, i.e., intravenously, intramuscularly or subcutaneously, intrathecally, transdermally (patch), by inhalation or intranasally.

Pharmaceutical compositions suitable for oral administration can be solids or liquids and can, for example, be in the form of tablets, pills, dragees, gelatin capsules, solutions, syrups, chewing-gums and the like.

To this end the active ingredient may be mixed with an inert diluent or a non-toxic pharmaceutically acceptable carrier such as starch or lactose. Optionally, these pharmaceutical compositions can also contain a binder such as microcrystalline cellulose, gum tragacanth or gelatine, a disintegrant such as alginic acid, a lubricant such as magnesium stearate, a glidant such as colloidal silicon dioxide, a sweetener such as sucrose or saccharin, or colouring agents or a flavouring agent such as peppermint or methyl salicylate.

The invention also contemplates compositions which can release the active substance in a controlled manner.

Pharmaceutical compositions which can be used for parenteral administration are in conventional form such as aqueous or oily solutions or suspensions generally contained in ampoules, disposable syringes, glass or plastics vials or infusion containers.

In addition to the active ingredient, these solutions or suspensions can optionally also contain a sterile diluent such as water for injection, a physiological saline solution, oils, polyethylene glycols, glycerine, propylene glycol or other synthetic solvents, antibacterial agents such as benzyl alcohol, antioxidants such as ascorbic acid or sodium bisulphite, chelating agents such as ethylene diamine-tetra-acetic acid, buffers such as acetates, citrates or phosphates and agents for adjusting the osmolarity, such as sodium chloride or dextrose.

These pharmaceutical forms are prepared using methods which are routinely used by pharmacists.

The amount of active ingredient in the pharmaceutical compositions can fall within a wide range of concentrations and depends on a variety of factors such as the patient's sex, age, weight and medical condition, as well as on the method of administration. Thus the quantity of compound of formula (I) in compositions for oral administration is at least 0.5% by weight and can be up to 80% by weight with respect to the total weight of the composition.

In accordance with the invention it has also been found that the compounds of formula (I) or the pharmaceutically acceptable salts thereof can be administered alone or in combination with other pharmaceutically active ingredients. Non-limiting examples of such additional compounds which can be cited for use in combination with the compounds according to the invention are antivirals, antispastics (e.g. baclofen), antiemetics, antimanic mood stabilizing agents, analgesics (e.g. aspirin, ibuprofen, paracetamol), narcotic analgesics, topical anesthetics, opioid analgesics, lithium salts, antidepressants (e.g. mianserin, fluoxetine, trazodone), tricyclic antidepressants (e.g. imipramine, desipramine), anticonvulsants (e.g. valproic acid, carbamazepine, phenyloin), antipsychotics (e.g. risperidone, haloperidol), neuroleptics, benzodiazepines (e.g. diazepam, clonazepam), phenothiazines (e.g. chlorpromazine), calcium channel blockers, amphetamine, clonidine, lidocaine, mexiletine, capsaicin, caffeine, quetiapine, serotonin antagonists, β-blockers, antiarrhythmics, triptans, ergot derivatives and amantadine.

For oral compositions, the daily dosage is in the range 1 mg to 2000 mg of compounds of formula I. For oral compositions the dosage unit is in the range 1 mg to 1000 mg of compounds of formula I, preferably 1 mg to 500 mg.

In compositions for parenteral administration, the quantity of compound of formula (I) present is at least 0.5% by weight and can be up to 33% by weight with respect to the total weight of the composition. For the preferred parenteral compositions, the dosage unit is in the range 1 mg to 2000 mg of compounds of formula I.

The daily dose can fall within a wide range of dosage units of compound of formula (I) and is generally in the range 1 to 2000 mg, preferably 1 to 1000 mg. However, it should be understood that the specific doses can be adapted to particular cases depending on the individual requirements, at the physician's discretion.

The SV2 proteins binding compounds provided by this invention and labeled derivatives thereof may be useful as standards and reagents in determining the ability of tested compounds (e.g., a potential pharmaceutical) to bind to the SV2 proteins.

Labeled derivatives of SV2 proteins' ligands provided by this invention may also be useful as radiotracers for positron emission tomography (PET) imaging or for single photon emission computerized tomography (SPECT).

The present invention therefore further provides labelled ligands as tools to screen chemical libraries for the discovery of potential pharmaceutical agents, in particular for treatment and prevention of the conditions set forth herein, on the basis of more potent binding to SV2 proteins, for localizing SV2 proteins in tissues, and for characterizing purified SV2 proteins. SV2 proteins include SV2A, SV2B, and SV2C whereby SV2A is the binding site for the anti-seizure drug levetiracetam and its analogs. The SV2 isoforms SV2A, SV2B, or SV2C can be derived from tissues, especially brain, from any mammal species, including human, rat or mice. Alternately the isoforms may be cloned versions of any mammalian species, including human, rat, and mice, heterologously expressed and used for assays. The screening method comprises exposing brain membranes, such as mammalian or human brain membranes, or cell lines expressing SV2 proteins or fragments thereof, especially SV2A and SV2C, but including SV2B, to a putative agent and incubating the membranes or proteins or fragments and the agent with labelled compound of formula I. The method further comprises determining if the binding of the compound of formula (I) to the protein is inhibited by the putative agent, thereby identifying binding partners for the protein. Thus, the screening assays enable the identification of new drugs or compounds that interact with SV2 proteins. The present invention also provides photoactivable ligands of SV2 proteins.

The labelled-ligands can also be used as tools to assess the conformation state of SV2 proteins after solubilization, purification and chromatography. The labelled-ligands may be directly or indirectly labeled. Examples of suitable labels include a radiolabel, such as $^3$H, a fluorescent label, an enzyme, europium, biotin and other conventional labels for assays of this type.

Labelled compounds of formula (I) are useful in the methods as probes in assays to screen for new compounds or agents that bind to the SV2 proteins (SV2A, SV2B and SV2C). In such assay embodiments, ligands can be used without modification or can be modified in a variety of ways; for example, by labelling, such as covalently or non-covalently joining a moiety which directly or indirectly provides a detectable signal. In any of these assays, the materials can be labelled either directly or indirectly. Possibilities for direct labelling include label groups such as: radiolabels including, but not limited to, [$^3$H], [$^{14}$C], [$^{32}$P], [$^{35}$S] or [$^{125}$I], enzymes such as peroxidase and alkaline phosphatase, and fluorescent labels capable of monitoring the change in fluorescence intensity, wavelength shift, or fluorescence polarization, including, but not limited to, fluorescein or rhodamine. Possibilities for indirect labelling include biotinylation of one constituent followed by binding to avidin coupled to one of the above label groups or the use of anti-ligand antibodies. The compounds may also include spacers or linkers in cases where the compounds are to be attached to a solid support. To identify agents or compounds which compete or interact with labelled ligands according to the invention for binding to the SV2 proteins (especially SV2A and SV2C), intact cells, cellular or membrane fragments containing SV2A or SV2C or the entire SV2 protein or a fragment thereof can be used. The agent or compound may be incubated with the cells, membranes, SV2 protein or fragment prior to, at the same time as, or after incubation with labelled levetiracetam or an analog or derivative thereof. Assays may be modified or prepared in any available format, including high-throughput screening (HTS) assays that monitor the binding of levetiracetam or the binding of derivatives or analogs thereof to SV2 proteins or fragments thereof. In many drug screening programs which test libraries of compounds, high throughput assays are desirable in order to maximize the number of compounds surveyed in a given period of time. Such screening assays may use intact cells, cellular or membrane fragments containing SV2 as well as cell-free or membrane-free systems, such as may be derived with purified or semi-purified proteins. The advantage of the assay with membrane fragment containing SV2 or purified SV2 proteins and peptides is that the effects of cellular toxicity and/or bioavailability of the test compound can be generally ignored, the assay instead being focused primarily on the effect of the drug on the molecular target as may be manifest in an inhibition of, for instance, binding between two molecules. The assay can be formulated to detect the ability of a test agent or compound to inhibit binding of labeled ligand according to the invention to SV2 or a fragment of SV2 or of labelled levetiracetam, or derivatives or analogs thereof, to SV2 or a fragment of SV2 protein. The inhibition of complex formation may be detected by a variety of techniques such as filtration assays, Flashplates (Perkin Elmer), scintillation proximity assays (SPA, GE). For high-throughput screenings (HTS), scintillation proximity assay which uses microspheres coated with biological membranes or flashplates coated with biological membranes are powerful methods that do not require separation or washing steps.

EXAMPLES

The following examples illustrate how the compounds covered by formula (I) may be synthesized. They are provided for illustrative purposes only and are not intended, nor should they be construed, as limiting the invention in any manner. Those skilled in the art will appreciate that routine variations and modifications of the following examples can be made without exceeding the spirit or scope of the invention.

NMR spectra are recorded on a BRUKER AVANCE 400 NMR Spectrometer fitted with a Linux workstation running XWIN NMR 3.5 software and a 5 mm inverse $^1$H/BB probehead, or BRUKER DRX 400 NMR fitted with a SG Fuel running XWIN NMR 2.6 software and a 5 mm inverse geometry $^1$H/$^{13}$C/$^{19}$F triple probehead. The compound is studied in $d_6$-dimethylsulfoxide (or $d_3$-chloroform) solution at a probe temperature of 313 K or 300 K and at a concentration of 10 mg/ml. The instrument is locked on the deuterium signal of $d_6$-dimethylsulfoxide (or $d_3$-chloroform). Chemical shifts are given in ppm downfield from TMS (tetramethylsilane) taken as internal standard.

HPLC analyses are performed using one of the following systems:
- an Agilent 1100 series HPLC system mounted with an INERTSIL ODS 3 C18, DP 5 µm, 250×4.6 mm column. The gradient runs from 100% solvent A (acetonitrile, water, phosphoric acid (5/95/0.001, v/v/v)) to 100% solvent B (acetonitrile, water, phosphoric acid (95/5/0.001, v/v/v)) in 6 min with a hold at 100% B of 4 min. The flow rate is set at 2.5 ml/min. The chromatography is carried out at 35° C.
- a HP 1090 series HPLC system mounted with a HPLC Waters Symetry C18, 250×4.6 mm column. The gradient runs from 100% solvent A (methanol, water, phosphoric acid (15/85/0.001M, v/v/M)) to 100% solvent B (methanol, water, phosphoric acid (85/15/0.001 M, v/v/M)) in 10 min with a hold at 100% B of 10 min. The flow rate is set at 1 ml/min. The chromatography is carried out at 40° C.

Mass spectrometric measurements in LC/MS mode are performed as follows:
HPLC Conditions
Analyses are performed using a WATERS Alliance HPLC system mounted with an INERTSIL ODS 3, DP 5 µm, 250×4.6 mm column.

The gradient runs from 100% solvent A (acetonitrile, water, trifluoroacetic acid (10/90/0.1, v/v/v)) to 100% solvent B (acetonitrile, water, trifluoroacetic acid (90/10/0.1, v/v/v)) in 7 min with a hold at 100% B of 4 min. The flow rate is set at 2.5 ml/min and a split of 1/25 is used just before API source.
MS Conditions Samples are dissolved in acetonitrile/water, 70/30, v/v at the concentration of about 250 µg/ml. API spectra (+ or −) are performed using a FINNIGAN LCQ ion trap mass spectrometer. APCI source operated at 450° C. and the capillary heater at 160° C. ESI source operated at 3.5 kV and the capillary heater at 210° C.

Mass spectrometric measurements in DIP/EI mode are performed as follows: samples are vaporized by heating the probe from 50° C. to 250° C. in 5 min. EI (Electron Impact) spectra are recorded using a FINNIGAN TSQ 700 tandem quadrupole mass spectrometer. The source temperature is set at 150° C.

Mass spectrometric measurements on a TSQ 700 tandem quadrupole mass spectrometer (Finnigan MAT) in GC/MS mode are performed with a gas chromatograph model 3400 (Varian) fitted with a split/splitless injector and a DB-5MS fused-silica column (15 m×0.25 mm I.D., 1 µm) from J&W Scientific. Helium (purity 99.999%) is used as carrier gas. The injector (CTC A200S autosampler) and the transfer line operate at 290 and 250° C., respectively. Sample (1 µl) is injected in splitless mode and the oven is temperature is programmed as follows: 50° C. for 5 min., increasing to 280° C. (23° C./min) and holding for 10 min. The TSQ 700 spectrometer operates in electron impact (EI) or chemical ionization (Cl/CH$_4$) mode (mass range 33-800, scan time 1.00 sec). The source temperature is set at 150° C.

High resolution mass spectrometry measurements are run on a Waters LCT Time of flight mass spectrometer equipped with an ESI source and a Waters Acquity UPLC (column: BEH C18 (1.7 µm, 2.1×50 mm)) with diode array detector. The gradient runs from 98% solvent A (aqueous ammonium formate (63 mg/l), 30% aqueous ammonia (50 µl/l)) to 95% acetonitrile and back in 6 min. The source parameters are as follows: ESI capillary voltage 2.5 kV, cone voltage 135 V, source block temperature 135° C., desolvation temperature 350° C., cone gas flow 20 L/Hr (Nitrogen), desolvation Gas flow 800 L/Hr. The detector is set with a flight tube at 7.2 KV and an MCP detector at 2,500 V. Specific rotation is recorded on a Perkin-Elmer 341 polarimeter. The angle of rotation is recorded at 25° C. on 1% solutions in methanol, at 589 nm.

Melting points are determined on a Büchi 535 or 545 Tottoli-type fusionometer, and are not corrected, or by the onset temperature on a Perkin Elmer DSC 7.

Preparative chromatographic separations are performed on silicagel 60 Merck, particle size 15-40 µm, reference 1.15111.9025, using Novasep axial compression columns (80 mm i.d.), flow rates between 70 and 150 ml/min. Amount of silicagel and solvent mixtures as described in individual procedures. Reverse phase separations are carried out using 500 g of either Kromasil C18 10 µm silicagel (acidic or neutral conditions) or Phenomenex Gemini C18 10 µM (basic conditions) in 8-cm ID columns with a flow rate of 150 ml/min. Products are detected at 215 nm unless otherwise specified.

Preparative Chiral Chromatographic separations are performed on a DAICEL Chiralpak AD 20 µm, 100*500 mm column using an in-house build instrument with various mixtures of lower alcohols and C5 to C8 linear, branched or cyclic alkanes at ±350 ml/min. Solvent mixtures as described in individual procedures.

Experiments requiring microwave irradiation are performed on a Biotage Initiator Sixty microwave oven upgraded with version 2.0 of the operating software. Experiments are run to reach the required temperature as quickly as possible (maximum irradiation power: 400 W, no external cooling).

Example 1

Synthesis of 1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one 5 and enantiomers 6 and 7

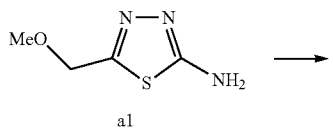

a1

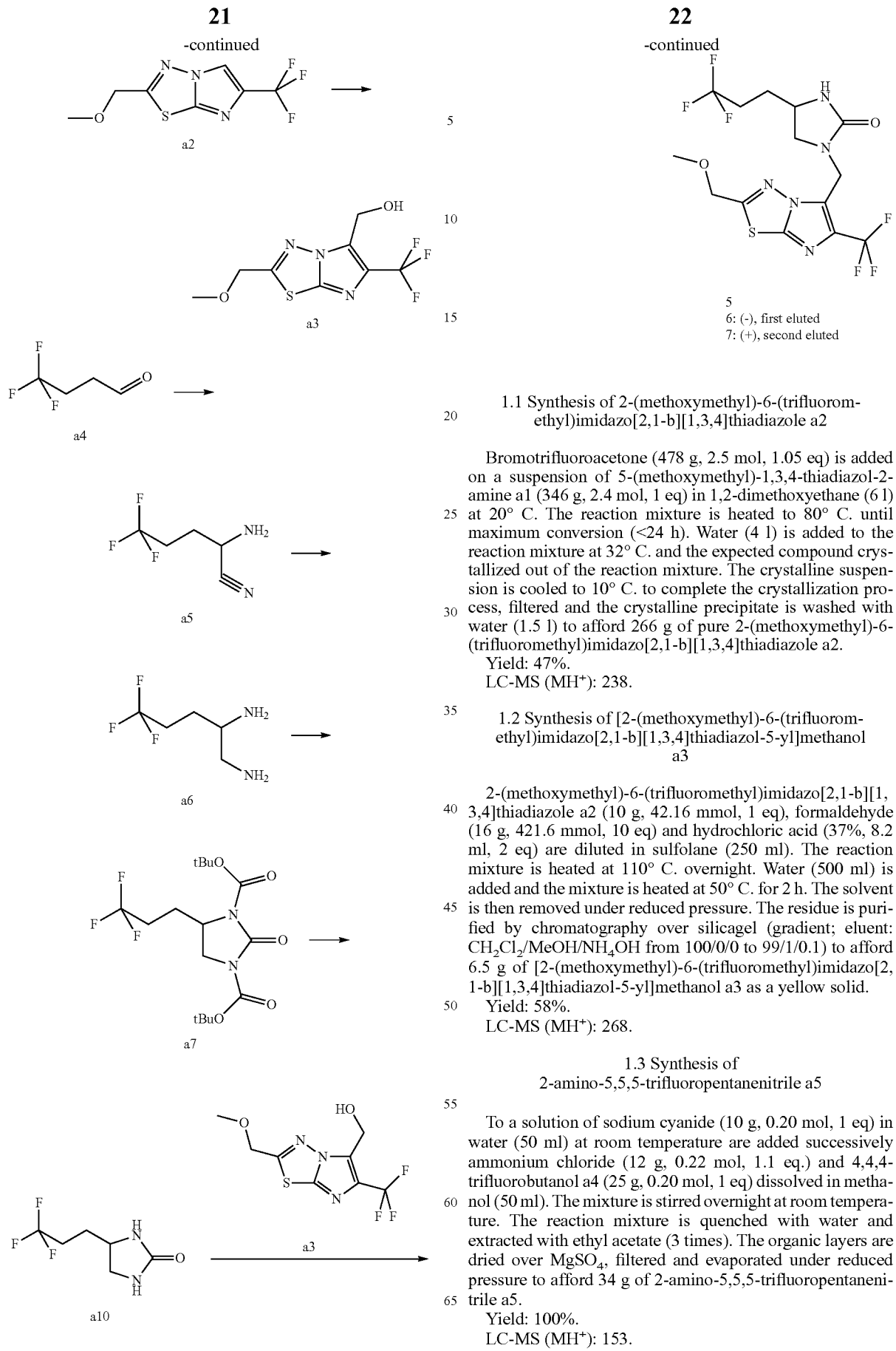

6: (−), first eluted
7: (+), second eluted 1.1 Synthesis of 2-(methoxymethyl)-6-(trifluoromethyl)imidazo[2,1-b][1,3,4]thiadiazole a2

Bromotrifluoroacetone (478 g, 2.5 mol, 1.05 eq) is added on a suspension of 5-(methoxymethyl)-1,3,4-thiadiazol-2-amine a1 (346 g, 2.4 mol, 1 eq) in 1,2-dimethoxyethane (6 l) at 20° C. The reaction mixture is heated to 80° C. until maximum conversion (<24 h). Water (4 l) is added to the reaction mixture at 32° C. and the expected compound crystallized out of the reaction mixture. The crystalline suspension is cooled to 10° C. to complete the crystallization process, filtered and the crystalline precipitate is washed with water (1.5 l) to afford 266 g of pure 2-(methoxymethyl)-6-(trifluoromethyl)imidazo[2,1-b][1,3,4]thiadiazole a2.
Yield: 47%.
LC-MS (MH$^+$): 238.

1.2 Synthesis of [2-(methoxymethyl)-6-(trifluoromethyl)imidazo[2,1-b][1,3,4]thiadiazol-5-yl]methanol a3

2-(methoxymethyl)-6-(trifluoromethyl)imidazo[2,1-b][1,3,4]thiadiazole a2 (10 g, 42.16 mmol, 1 eq), formaldehyde (16 g, 421.6 mmol, 10 eq) and hydrochloric acid (37%, 8.2 ml, 2 eq) are diluted in sulfolane (250 ml). The reaction mixture is heated at 110° C. overnight. Water (500 ml) is added and the mixture is heated at 50° C. for 2 h. The solvent is then removed under reduced pressure. The residue is purified by chromatography over silicagel (gradient; eluent: CH$_2$Cl$_2$/MeOH/NH$_4$OH from 100/0/0 to 99/1/0.1) to afford 6.5 g of [2-(methoxymethyl)-6-(trifluoromethyl)imidazo[2,1-b][1,3,4]thiadiazol-5-yl]methanol a3 as a yellow solid.
Yield: 58%.
LC-MS (MH$^+$): 268.

1.3 Synthesis of 2-amino-5,5,5-trifluoropentanenitrile a5

To a solution of sodium cyanide (10 g, 0.20 mol, 1 eq) in water (50 ml) at room temperature are added successively ammonium chloride (12 g, 0.22 mol, 1.1 eq.) and 4,4,4-trifluorobutanol a4 (25 g, 0.20 mol, 1 eq) dissolved in methanol (50 ml). The mixture is stirred overnight at room temperature. The reaction mixture is quenched with water and extracted with ethyl acetate (3 times). The organic layers are dried over MgSO$_4$, filtered and evaporated under reduced pressure to afford 34 g of 2-amino-5,5,5-trifluoropentanenitrile a5.
Yield: 100%.
LC-MS (MH$^+$): 153.

1.4 Synthesis of 5,5,5-trifluoropentane-1,2-diamine a6

2-amino-5,5,5-trifluoropentanenitrile a5 (34 g, 2.2 mol, 1 eq) is dissolved in tetrahydrofurane (290 ml). Lithium aluminium hydride (25.5 g, 6.7 mol, 3 eq) is then added portionwise at 0° C. The reaction mixture is heated at 60° C. for 2 hours, then stirred overnight at room temperature. Disodium sulfate decahydrate (6 eq) is added portionwise and the mixture is stirred until the appearance of a white solid. The precipitate is filtered and the organic phase is condensed under vacuum to afford 11.2 g of 5,5,5-trifluoropentane-1,2-diamine a6 as orange oil.

Yield: 32%.

LC-MS (M1-1±): 157.

1.5 Synthesis of di-tert-butyl 2-oxo-4-(3,3,3-trifluoropropyl)imidazolidine-1,3-dicarboxylate a7

Di-tert-butyl dicarbonate (54.6 g, 2.5 mol, 3.5 eq) and 4-dimethylaminopyridine (4.37 g, 0.357 mol, 0.5 eq) are successively added at room temperature to a solution of 5,5,5-trifluoropentane-1,2-diamine a6 (11.17 g, 0.72 mol, 1 eq) in acetonitrile (430 ml). The mixture is stirred overnight. The reaction mixture is extracted with ethyl acetate (3 times), the combined organic layers are washed with water and brine, then dried over $MgSO_4$, and condensed under reduced pressure. The residue is purified by chromatography over silicagel (eluent: $CH_2Cl_2/MeOH/NH_4OH$ 99.5/0.45/0.05) to afford 6.76 g of di-tert-butyl 2-oxo-4-(3,3,3-trifluoropropyl)imidazolidine-1,3-dicarboxylate a7.

Yield: 25%.

LC-MS ($MH^+$): 383.

The following compounds may be synthesized according to the same method:

| | | |
|---|---|---|
| a8 | di-tert-butyl 2-oxo-4-propylimidazolidine-1,3-dicarboxylate | LC-MS ($MH^+$): 329 |
| a9 | di-tert-butyl 4-(2-methylpropyl)-2-oxoimidazolidine-1,3-dicarboxylate | LC-MS ($MH^+$): 343 |

1.6 Synthesis of 4-(3,3,3-trifluoropropyl)imidazolidin-2-one a10

Trifluoroacetic acid (6.05 g, 53.04 mmol, 3 eq) in dichloromethane (50 ml) is added to a solution of di-tert-butyl 2-oxo-4-(3,3,3-trifluoropropyl)imidazolidine-1,3-dicarboxylate a7 (6.76 g, 17.68 mmol, 1 eq) in dichloromethane (60 ml) at room temperature overnight. The reaction mixture is condensed under reduced pressure to afford 4.22 g of 4-(3,3,3-trifluoropropyl)imidazolidin-2-one a10 as a yellow oil.

Yield: 100%.

LC-MS ($MH^+$): 183.

The following compounds may be synthesized according to the same method:

| | | |
|---|---|---|
| a11 | 4-propylimidazolidin-2-one | LC-MS ($MH^+$): 129 |
| a12 | 4-(2-methylpropyl)imidazolidin-2-one | LC-MS ($MH^+$): 143 |

1.7 Synthesis of 1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one 5 and enantiomers 6 and 7

[2-(methoxymethyl)-6-(trifluoromethyl)imidazo[2,1-b][1,3,4]thiadiazol-5-yl]methanol a3 (3.26 g, 0.122 mol, 1 eq) and p-toluenesulphonic acid (2.10 g, 0.122 mol, 1 eq) are successively added to a solution of 4-(3,3,3-trifluoropropyl)imidazolidin-2-one a10 (2.22 g, 0.122 mol, 1 eq) in toluene (450 ml). The mixture is heated at 110° C. overnight. The reaction is not complete and another portion of intermediate a10 (1 g, 5.49 mmol, 0.45 eq) is added. The mixture is heated at 110° C. overnight, then the solvent is evaporated under reduced pressure. Water is added to the residue, the mixture is extracted with $CH_2Cl_2$, the organic layer is dried over $MgSO_4$, filtered and condensed under reduced pressure. The residue is purified by chromatography over silicagel (eluent: $CH_2Cl_2/MeOH/NH_4OH$ 98/2/0.2) to afford 336 mg of 1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one 5 as a yellow oil.

Yield: 64%.

LC-MS ($MH^+$): 432.

Compounds 1 and 2 may be synthesized according to the same method.

Enantiomers of 1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one 5 are separated by chiral chromatography (Phase: Chiralpak IC; 30° C.; eluent n-heptane/isopropanol 50/50).

Pure (−)-1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one 6 (first eluted, 70 mg) is obtained after recrystallization in $Et_2O$/Hexane 50/50.

Yield: 21%.

LC-MS ($MH^+$): 432.

Pure (+)-1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one 7 (second eluted, 55 mg) is obtained after recrystallization in $Et_2O$/Hexane 50/50.

Yield: 16%.

LC-MS ($MH^+$): 432.

Compounds 3 and 4 may be obtained according to the same method.

Enantiomers of 1-{[2-(methoxymethyl)-6-(trifluoromethyl)imidazo[2,1-b][1,3,4]thiadiazol-5-yl]methyl}-4-(2-methylpropyl)imidazolidin-2-one 1 (285 mg) are separated by chiral chromatography (Phase: Chiralpak AD; 30° C.; eluent n-heptane/ethanol/diethylamine 90/10/0.01).

Pure (−)-1-{[2-(methoxymethyl)-6-(trifluoromethyl)imidazo[2,1-b][1,3,4]thiadiazol-5-yl]methyl}-4-(2-methylpropyl)imidazolidin-2-one 20 (first eluted, 94 mg) is obtained after recrystallization in $CH_2Cl_2$/Hexane 50/50.

Yield: 33%. LC-MS ($MH^+$): 392.

Pure (+)-1-{[2-(methoxymethyl)-6-(trifluoromethyl)imidazo[2,1-b][1,3,4]thiadiazol-5-yl]methyl}-4-(2-methylpropyl)imidazolidin-2-one 21 (second eluted, 68 mg) is obtained after recrystallization in $CH_2Cl_2$/Hexane 50/50.

Yield: 24%. LC-MS ($MH^+$): 392.

Example 2

Synthesis of 1-{[6-chloro-2-(methoxymethyl)imidazo[2,1-b][1,3,4]-thiadiazol-5-yl]methyl}-4-(3,3,3-trifluoropropyl)imidazolidin-2-one 8 and enantiomers 9 and 10

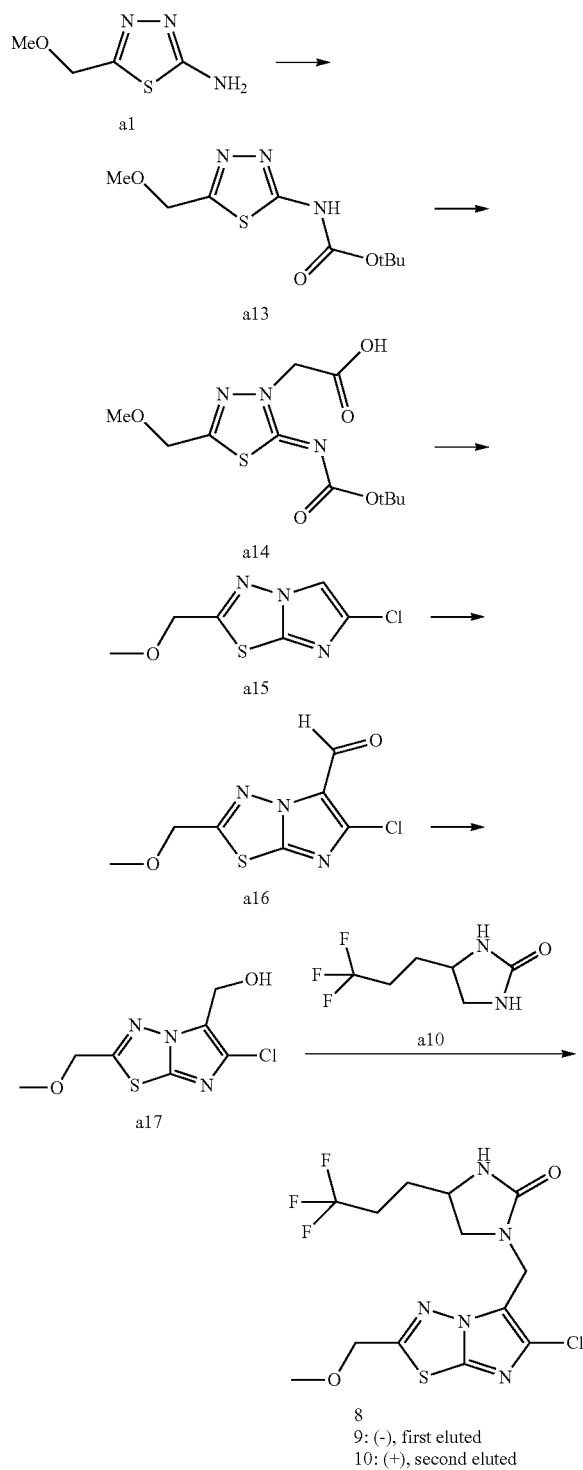

8
9: (−), first eluted
10: (+), second eluted

2.1 Synthesis of tert-butyl [5-(methoxymethyl)-1,3,4-thiadiazol-2-yl]carbamate a13

To a suspension of 5-(methoxymethyl)-1,3,4-thiadiazol-2-amine a1 (100 g, 0.69 mol, 1 eq) in dichloromethane (1 l) at room temperature are added, successively and each in one portion, di-tert-butyl dicarbonate (132 g, 0.76 mol, 1.1 eq,) and N,N-dimethylaminopyridine (8.35 g, 0.069 mol, 0.1 eq). After overnight stirring at room temperature, the reaction mixture is washed with 1N HCl (pH 5) to remove N,N-dimethylaminopyridine. The solvent is removed under reduced pressure and the residue is recrystallized from di-isopropyl ether to afford 148.9 g of pure tert-butyl [5-(methoxymethyl)-1,3,4-thiadiazol-2-yl]carbamate a13.

Yield: 88%. LC-MS (MH$^+$): 246.

2.2 Synthesis of {2-[(tert-butoxycarbonyl)imino]-5-(methoxymethyl)-1,3,4-thiadiazol-3(2H)-yl}acetic acid a14

Iodoacetic acid (409.3 g, 2.2 mol, 1.5 eq) is added in one portion to a solution of tert-butyl [5-(methoxymethyl)-1,3,4-thiadiazol-2-yl]carbamate a13 (360 g, 1.47 mol, 1 eq) in tetrahydrofurane (3 l) at room temperature. Sodium hydride (52.8 g, 2.2 mol, 1.5 eq) is then added portionwise, in 30 minutes, at room temperature. The reaction mixture is heated at 60° C. overnight, and the solvent is evaporated under reduced pressure. Water is added to the residue, the solution is acidified to pH=2 with aqueous 6N HCl, then extracted with CH$_2$Cl$_2$. The organic layer is washed with 10% aqueous sodium thiosulfate and evaporated to dryness to afford 455.7 g of {2-[(tert-butoxy-carbonyl)imino]-5-(methoxymethyl)-1,3,4-thiadiazol-3(2H)-yl}acetic acid a14 which is used directly in the next step without any further purification.

Yield: 90%. LC-MS (MH$^+$): 304.

2.3 Synthesis of 6-chloro-2-(methoxymethyl)imidazo[2,1-b][1,3,4]thiadiazole a15

To {2-[(tert-butoxycarbonyl)imino]-5-(methoxymethyl)-1,3,4-thiadiazol-3(2H)-yl}acetic acid a14 (418 g, 1.38 mol, 1 eq) in acetonitrile (2.5 l) at room temperature, are successively and slowly added triethyl amine (278.9 g, 2.76 mol, 2 eq), then phosphorous oxychloride (633.9 g, 4.13 mol, 3 eq). The reaction mixture is heated at 80° C. for one hour. After reaction completion, water (2.2 l) is slowly and carefully added at 50° C. The reaction mixture is extracted with dichloromethane (2×1.2 l), the combined organic layers are washed by a NaOH/NaCl aqueous solution (1.4 l of saturated NaCl solution+400 ml 2N NaOH), dried over MgSO$_4$, filtered and condensed under reduced pressure. The residue is recrystallized from acetonitrile/water (1/1) to afford 99.8 g of pure 6-chloro-2-(methoxymethyl)imidazo[2,1-b][1,3,4]thiadiazole a15.

Yield: 36%. LC-MS (MH$^+$): 204/206.

2.4 Synthesis of 6-chloro-2-(methoxymethyl)imidazo[2,1-b][1,3,4]thiadiazole-5-carbaldehyde a16

Phosphorus oxychloride (2.75 ml, 3 eq) is added very slowly to dimethyl formamide (5 ml) cooled at 0° C. The temperature rises to 50° C. The reaction mixture is heated at 60° C., then 6-chloro-2-(methoxymethyl)imidazo[2,1-b][1,3,4]thiadiazole a15 (2 g, 9.82 mmol, 1 eq) is added portionwise for 2.5 h. The reaction mixture is poured on an ice/water mixture. The precipitate is filtered and washed with water.

The residue is dried overnight at 40° C. under reduced pressure to afford 1.8 g of 6-chloro-2-(methoxymethyl)imidazo[2,1-b][1,3,4]thiadiazole-5-carbaldehyde a16 as a solid.

Yield: 79%.

LC-MS (MH+): 232/234.

2.5 Synthesis of [6-chloro-2-(methoxymethyl)imidazo[2,1-b][1,3,4]thiadiazol-5-yl]-methanol a17

6-chloro-2-(methoxymethyl)imidazo[2,1-b][1,3,4]thiadiazole-5-carbaldehyde a16 (2.97 g, 12.94 mmol, 1 eq) is dissolved in ethanol (80 ml), cooled at 0° C. and sodium borohydride (578 mg, 15.53 mmol, 1.2 eq) is added portionwise at 0° C. The reaction mixture is stirred overnight at room temperature, then cooled at 0° C. and a saturated NH₄Cl aqueous solution (100 ml) is added. The organic solvent is evaporated under reduced pressure and the precipitate is filtered, dried under vacuum at 20° C. to afford 1.99 g of [6-chloro-2-(methoxymethyl)imidazo[2,1-b][1,3,4]thiadiazol-5-yl]methanol a17.

Yield: 66%. LC-MS (MH+): 234/236.

2.6 Synthesis of 1-{[6-chloro-2-(methoxymethyl)imidazo[2,1-b][1,3,4]thiadiazol-5-yl]methyl}-4-(3,3,3-trifluoropropyl)imidazolidin-2-one 8 and enantiomers 9 and 10

1-{[6-chloro-2-(methoxymethyl)imidazo[2,1-b][1,3,4]thiadiazol-5-yl]methyl}-4-(3,3,3-trifluoropropyl)imidazolidin-2-one 8 and enantiomers may be prepared according to the method described in example 1.7.

Compound 8:

Yield: 3%. LC-MS (MH+): 398/400.

Compound 9: first eluted, (+1-{[6-chloro-2-(methoxymethyl)imidazo[2,1-b][1,3,4]thiadiazol-5-yl]methyl}-4-(3,3,3-trifluoropropyl)imidazolidin-2-one:

Yield: 15%. LC-MS (MH+): 398/400.

Compound 10: second eluted, (+)-1-{[6-chloro-2-(methoxymethyl)imidazo[2,1-b][1,3,4]thiadiazol-5-yl]methyl}-4-(3,3,3-trifluoropropyl)imidazolidin-2-one:

Yield: 7%. LC-MS (MH+): 398/400.

Example 3

Synthesis of 1-{[2-(methoxymethyl)-6-(trifluoromethyl)imidazo[2,1-b][1,3,4]thiadiazol-5-yl]methyl}-4-(2,2,2-trifluoroethyl)imidazolidin-2-one 11 and enantiomers, 4-(2-chloro-2,2-difluoroethyl)-1-{[2-(methoxymethyl)-6-(trifluoro-methyl)imidazo[2,1-b][1,3,4]thiadiazol-5-yl]methyl}imidazolidin-2-one 12 and enantiomers, and 4-(2,2-difluoroethenyl)-1-{[2-(methoxymethyl)-6-(trifluoromethyl)-imidazo[2,1-b][1,3,4]thiadiazol-5-yl]methyl}imidazolidin-2-one 17

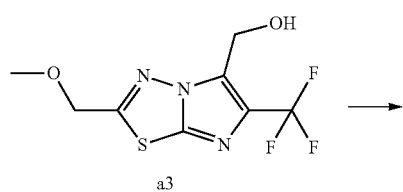

a3

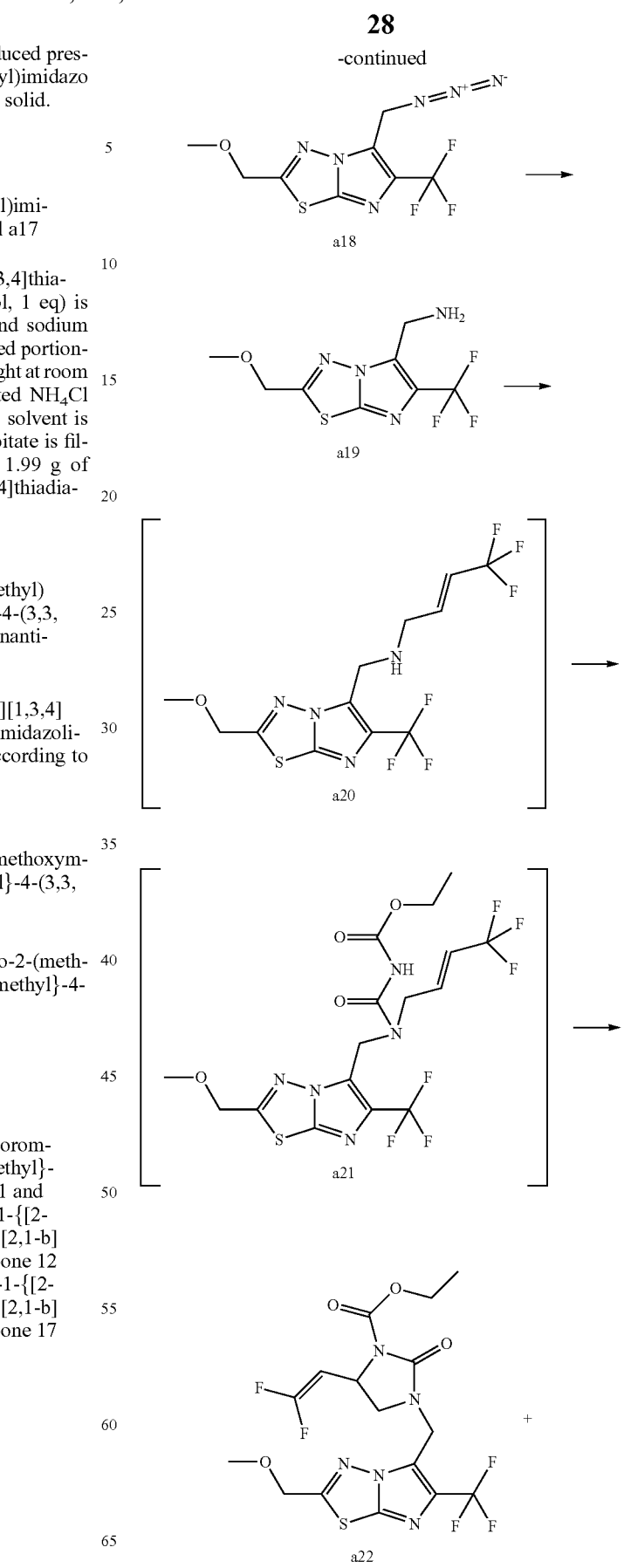

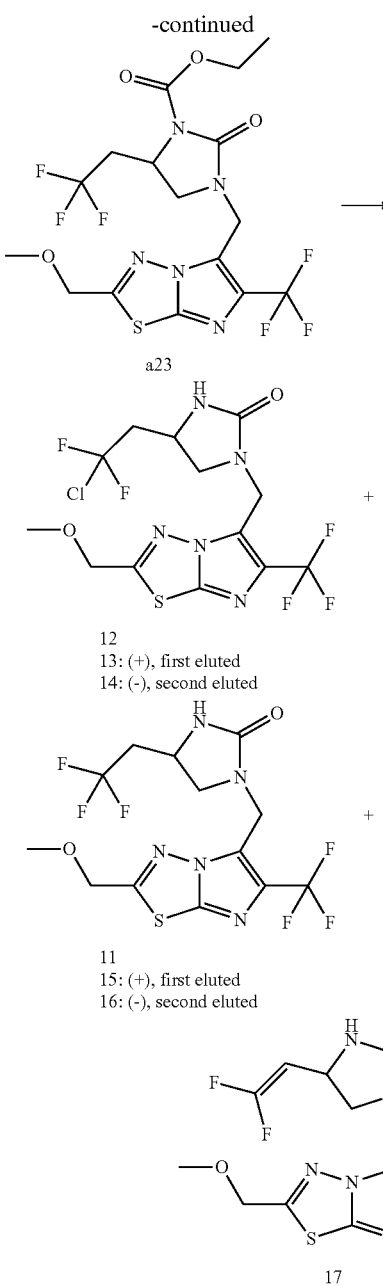

12
13: (+), first eluted
14: (-), second eluted 11
15: (+), first eluted
16: (-), second eluted

17

3.1 Synthesis of 5-(azidomethyl)-2-(methoxymethyl)-6-(trifluoromethyl)imidazo[2,1-b][1,3,4]thiadiazole a18

N,N-Diisopropylethylamine (3.22 g, 24.88 mmol, 5 eq) and methanesulfonyl chloride (0.855 g, 7.47 mmol, 1.5 eq) are successively and slowly added at 0° C. to a solution of [2-(methoxymethyl)-6-(trifluoromethyl)imidazo[2,1-b][1,3,4]thiadiazol-5-yl]methanol a3 (1.33 g, 4.98 mmol, 1 eq) in dichloromethane (30 ml). Sodium azide (0.485 g, 7.47 mmol, 1.5 eq) in suspension in DMF (5 ml) is added at 0° C., then warmed up to room temperature and the reaction mixture is stirred overnight. After hydrolysis ($H_2O$) and extraction with diethylether, the combined organic layers are dried over $MgSO_4$, filtered and evaporated under reduced pressure to afford 1.45 g of 5-(azidomethyl)-2-(methoxymethyl)-6-(trifluoromethyl)imidazo[2,1-b][1,3,4]thiadiazole a18.

Yield: 100%. LC-MS (MH$^+$): 293.

3.2 Synthesis of 1-[2-(methoxymethyl)-6-(trifluoromethyl)imidazo[2,1-b][1,3,4]thiadiazol-5-yl]methanamine a19

Triphenylphosphine (1.31 g, 4.98 mmol, 1 eq) is added at room temperature to a suspension of 5-(azidomethyl)-2-(methoxymethyl)-6-(trifluoromethyl)imidazo[2,1-b][1,3,4]thiadiazole a18 (1.45 g, 4.98 mmol, 1 eq) in THF/$H_2O$ (18 ml/2 ml). The reaction mixture is stirred at room temperature for 60 h. The solvent is evaporated under reduced pressure, water is added to the residue, the solution is acidified to pH 2 with aqueous 5N HCl, then extracted with $Et_2O$ (1×50 ml). The aqueous layer is basified (pH 8) by addition of a $Na_2CO_3$ aqueous solution, and extracted with dichloromethane (2×50 ml), the cumulated organics layers are dried over $MgSO_4$, filtered and evaporated under reduced pressure to afford 1-[2-(methoxymethyl)-6-(trifluoromethyl)imidazo[2,1-b][1,3,4]thiadiazol-5-yl]methanamine a19.

Yield: 88%. LC-MS (MH$^+$): 267.

3.3 Synthesis of ethyl 5-(2,2-difluoroethenyl)-3-{[2-(methoxymethyl)-6-(trifluoro-methyl)imidazo[2,1-b][1,3,4]thiadiazol-5-yl]methyl}-2-oxoimidazolidine-1-carboxylate a22

4-bromo-1,1,1-trifluorobut-2-ene (0.782 g, 4.14 mmol, 1.4 eq) and sodium carbonate (0.376 g, 3.55 mmol, 1.2 eq) are added to suspension of 1-[2-(methoxymethyl)-6-(trifluoromethyl)imidazo[2,1-b][1,3,4]thiadiazol-5-yl]methanamine a19 in N,N-dimethylformamide (15 ml). The mixture is stirred overnight at room temperature to afford crude 4,4,4-trifluoro-N-{[2-(methoxymethyl)-6-(trifluoromethyl)imidazo[2,1-b][1,3,4]thiadiazol-5-yl]methyl}but-2-en-1-amine a20. Ethoxycarbonyl isocyanate (0.51 g, 4.43 mmol, 1.5 eq) is added to the reaction mixture. After 4 h, the reaction is not complete and ethoxycarbonyl isocyanate (0.5 eq) is added again. The reaction mixture is stirred overnight to afford crude ethyl ({[2-(methoxymethyl)-6-(trifluoromethyl)imidazo[2,1-b][1,3,4]thiadiazol-5-yl]methyl}[(4,4,4-trifluorobut-2-en-1-yl]carbamoyl)carbamate a21. Potassium tert-butoxide is added and the reaction mixture is heated at 75° C. for 4 h. After cooling, the reaction mixture is extracted with toluene (2×80 ml). The cumulated organic layers are dried over $MgSO_4$, filtered and condensed under reduced pressure. The residue is purified by chromatography over silicagel (eluent: $CH_2Cl_2$/MeOH 99/1) to afford 602 mg of a mixture of ethyl 5-(2,2-difluoroethenyl)-3-{[2-(methoxymethyl)-6-(trifluoromethyl)imidazo[2,1-b][1,3,4]thiadiazol-5-yl]methyl}-2-oxoimidazolidine-1-carboxylate a22 (as the major compound) and ethyl 3-{[2-(methoxymethyl)-6-(trifluoromethyl)imidazo[2,1-b][1,3,4]thiadiazol-5-yl]methyl}-2-oxo-5-(2,2,2-trifluoroethyl)imidazolidine-1-carboxylate a23.

Yield: estimated at 43%.
Compound a22: LC-MS (MH$^+$): 470.
Compound a23: LC-MS (MH$^+$): 490.

3.4 Synthesis of 1-{[2-(methoxymethyl)-6-(trifluoromethyl)imidazo[2,1-b][1,3,4]thia-diazol-5-yl]methyl}-4-(2,2,2-trifluoroethyl)imidazolidin-2-one 11 and enantiomers 15 and 16, 4-(2-chloro-2,2-difluoroethyl)-1-{[2-(methoxymethyl)-6 5-(trifluoromethyl)imidazo[2,1-b][1,3,4]thia-diazol-5-yl]methyl}imidazolidin-2-one 12 and enantiomers 13 and 14, and 4-(2,2-difluoroethenyl)-1-{[2-(methoxymethyl)-6-(trifluoromethyl)-imidazo[2,1-b][1,3,4]thiadiazol-5-yl]methyl}imidazolidin-2-one 17

A suspension of the mixture of compounds a22 and a23 obtained previously (600 mg, 1.28 mmol) in THF/HCl 37%

(10 ml/15 ml) is heated at 80° C. for seven days. After cooling and neutralization by sodium carbonate, the reaction mixture is extracted with CH$_2$Cl$_2$ (2×80 ml), dried over MgSO$_4$, filtered and condensed under reduced pressure. The residue is purified by chromatography over silicagel (eluent: CH$_2$Cl$_2$/ MeOH 99/1) to afford three different fractions.

The first fraction is evaporated to afford 213 mg of 4-(2-chloro-2,2-difluoroethyl)-1-{[2-(methoxymethyl)-6-(trifluoromethyl)imidazo[2,1-b][1,3,4]thiadiazol-5-yl] methyl}imidazolidin-2-one 12.

Yield: 45%. LC-MS (MH$^+$): 434.

The second fraction is evaporated and purified by reverse phase chromatography (basic conditions; gradient; eluent: H$_2$O/CH$_3$CN/NH$_4$CO$_3$/NH$_4$OH 95/5/0.1/0.005 to 40/60/0.1/ 0.005; 7 min) to afford 8 mg of 1-{[2-(methoxymethyl)-6-(trifluoromethyl)-imidazo[2,1-b][1,3,4]thiadiazol-5-yl]methyl}-4-(2,2,2-trifluoroethyl)imidazolidin-2-one 11.

LC-MS (MH$^+$): 418.

The third fraction is evaporated and purified by reverse phase chromatography (basic conditions; gradient; eluent: H$_2$O/CH$_3$CN/NH$_4$OH 60/40/0.1 to 30/70/0.1; 10 min) to afford 8 mg of 4-(2,2-difluoroethenyl)-1-{[2-(methoxymethyl)-6-(trifluoromethyl)imidazo[2,1-b][1,3,4]thiadiazol-5-yl]methyl}imidazolidin-2-one 17.

LC-MS (MH$^+$): 398.

The enantiomers of 4-(2-chloro-2,2-difluoroethyl)-1-{[2-(methoxymethyl)-6-(trifluoro-methyl)imidazo[2,1-b][1,3,4] thiadiazol-5-yl]methyl}imidazolidin-2-one 12 are separated by chiral chromatography (phase: Chiralpak AS-V; 30° C.; column 50*490 mm; eluent: isopropanol/n-heptane 50/50)

Pure (+)-4-(2-chloro-2,2-difluoroethyl)-1-{[2-(methoxymethyl)-6-(trifluoromethyl) imidazo-[2,1-b][1,3,4]thiadiazol-5-yl]methyl}imidazolidin-2-one 13 (first eluted, 35 mg) is obtained after recrystallization in CH$_2$Cl$_2$/Hexane.

Yield: 16%. LC-MS (MH$^+$): 434/436.

Pure (−)-4-(2-chloro-2,2-difluoroethyl)-1-{[2-(methoxymethyl)-6-(trifluoromethyl) imidazo-[2,1-b][1,3,4]thiadiazol-5-yl]methyl}imidazolidin-2-one 14 (second eluted, 32 mg) is obtained after recrystallization in CH$_2$Cl$_2$/Hexane.

Yield: 15%. LC-MS (MH$^+$): 434/436.

The enantiomers of 1-{[2-(methoxymethyl)-6-(trifluoromethyl)-imidazo[2,1-b][1,3,4]-thiadiazol-5-yl]methyl}-4-(2,2,2-trifluoroethyl)imidazolidin-2-one 11 (130 mg) are separated by chiral chromatography (phase: Chiralpak AS-V; 30° C.; column 50*490 mm; eluent: isopropanol/n-heptane 50/50)

Pure (+)-1-{[2-(methoxymethyl)-6-(trifluoromethyl)-imidazo[2,1-b][1,3,4]thiadiazol-5-yl]methyl}-4-(2,2,2-trifluoroethyl)imidazolidin-2-one 15 (first eluted, 65 mg) is obtained after recrystallization in CH$_2$Cl$_2$/Hexane.

Yield: 50%. LC-MS (MH$^{+D}$: 418.

Pure (−)-1-{[2-(methoxymethyl)-6-(trifluoromethyl)-imidazo[2,1-b][1,3,4]thiadiazol-5-yl]methyl}-4-(2,2,2-trifluoroethyl)imidazolidin-2-one 16 (second eluted, 63 mg) is obtained after recrystallization in CH$_2$Cl$_2$/Hexane.

Yield: 48%. LC-MS (MH$^{-1-}$): 418.

Example 4

Synthesis of 4-(2-chloro-2,2-difluoroethyl)-1-{[2-(hydroxymethyl)-6-(trifluoromethyl)imidazo[2,1-b] [1,3,4]-thiadiazol-5-yl]methyl}imidazolidin-2-one 18

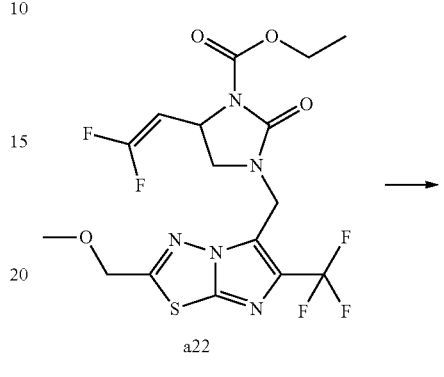

a22

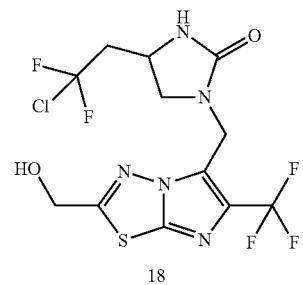

18

HCl (37%, 4 ml) is added to ethyl 5-(2,2-difluoroethenyl)-3-{[2-(methoxymethyl)-6-(trifluoromethyl)imidazo[2,1-b] [1,3,4]thiadiazol-5-yl]methyl}-2-oxoimidazolidine-1-carboxylate a22 (226 mg, 0.48 mmol) at room temperature then stirred at 100° C. for 60 h. After cooling and neutralization by sodium carbonate, the reaction mixture is extracted with CH$_2$Cl$_2$ (2×30 ml), dried over MgSO$_4$, filtered and condensed under reduced pressure. The residue is purified by chromatography (basic conditions; gradient; eluent: H$_2$O/CH$_3$CN/ NH$_4$CO$_3$/NH$_4$OH 95/5/0.1/0.005 to 40/60/0.1/0.005; 7 min) to afford 25 mg of pure 4-(2-chloro-2,2-difluoroethyl)-1-{[2-(hydroxymethyl)-6-(trifluoromethyl)-imidazo[2,1-b][1,3,4] thiadiazol-5-yl]methyl}imidazolidin-2-one 18.

Yield: 12%. LC-MS (MH$^+$): 420/422.

Compound 19 may be synthesized according to the same method starting from a23.

Example 5

Synthesis of (+)-4-(2-chloro-2,2-difluoroethyl)-1-{[2-(methoxymethyl)-6-(trifluoromethyl)imidazo[2,1-b][1,3,4]thiadiazol-5-yl]methyl}-3-methylimidazolidin-2-one 22

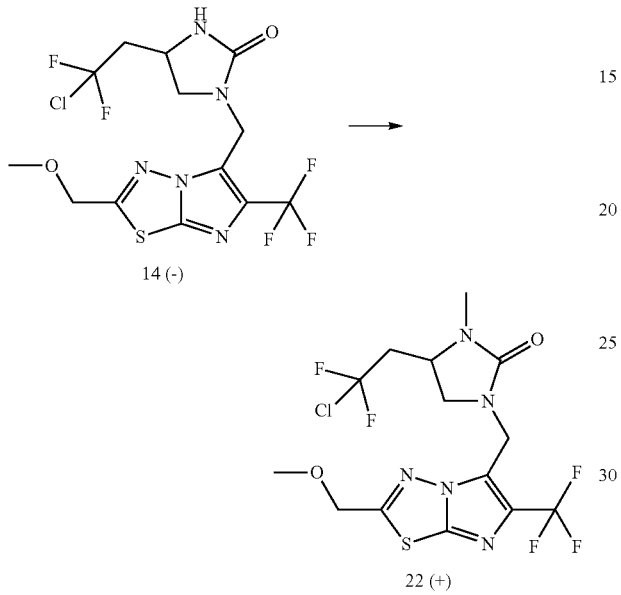

To a solution of (+4-(2-chloro-2,2-difluoroethyl)-1-{[2-(methoxymethyl)-6-(trifluoro-methyl)imidazo[2,1-b][1,3,4]thiadiazol-5-yl]methyl}imidazolidin-2-one 14 (120 mg, 0.277 mmol) in $CH_2Cl_2$ (12 ml) is added, at 0° C., sodium hydroxide (3.96 ml, 1M solution), tetrabutylammonium bromide (82 mg, 0.1 eq.) and iodomethane (0.035 ml, 2 eq.). The mixture is stirred at room temperature for 120 h. Iodomethane (0.060 ml) is added and the mixture is stirred at room temperature for 24 h. Iodomethane is added (2×0.060 ml) and the mixture is stirred for 72 h. Water is added and the reaction mixture is extracted with $CH_2Cl_2$ (2 times), dried over $MgSO_4$, filtered and condensed under reduced pressure. The residue is purified by chromatography (basic conditions; gradient; eluent: $H_2O/CH_3CN/NH_4OH$ 60/40/0.1 to 30/70/0.1; 10 min) to afford 54 mg of pure (+)-4-(2-chloro-2,2-difluoroethyl)-1-{[2-(methoxymethyl)-6-(trifluoromethyl) imidazo[2,1-b][1,3,4]-thiadiazol-5-yl]methyl}-3-methylimidazolidin-2-one 22.

Yield: 43%. LC-MS (MH$^+$): 448/450.

Compound 23 may be synthesized according to the same method starting from (+)-4-(2-chloro-2,2-difluoroethyl)-1-{[2-(methoxymethyl)-6-(trifluoromethyl)imidazo[2,1-b][1,3,4]thiadiazol-5-yl]methyl}imidazolidin-2-one 13.

Table (I) indicates the IUPAC name of the compound, the ion peak observed in mass spectroscopy, the $^1$H NMR description, the melting point or onset on DSC, and the alphaD.

TABLE I

Physical Characterization of Example Compounds.

| n° | IUPAC NAME | MN$^+$ | $^1$H NMR δ (DMSO) | alpha$_D$ |
|---|---|---|---|---|
| 1 | 1-{[2-(methoxymethyl)-6-(trifluoromethyl)imidazo[2,1-b][1,3,4]thiadiazol-5-yl]methyl}-4-(2-methylpropyl)imidazolidin-2-one | 392 | 6.76 (s, 1H), 4.84 (s, 2H), 4.62 (dd, 2H), 3.52 (quint, 1H, J = 7.1 Hz), 3.44 (s, 3H), 3.37 (m, 1H), 3.31 (s, 1H), 2.80 (t, 1H, J = 7.7 Hz), 1.58 (m, 1H), 1.32 (m, 1H), 1.18 (m, 1H), 0.81 (t, 6H, J = 6.1 Hz) | |
| 2 | 1-{[2-(methoxymethyl)-6-(trifluoromethyl)imidazo[2,1-b][1,3,4]thiadiazol-5-yl]methyl}-4-propylimidazolidin-2-one | 378 | — | |
| 3 | (−)-1-{[2-(methoxymethyl)-6-(trifluoromethyl)imidazo[2,1-b][1,3,4]thiadiazol-5-yl]methyl}-4-propylimidazolidin-2-one | 378 | 6.76 (s, 1H), 4.84 (s, 2H), 4.62 (dd, 2H, J = 69.8, 15.5 Hz), 3.44 (s, 4H), 3.35 (m, 1H), 2.81 (t, 1H, J = 7.8 Hz), 1.26 (m, 4H), 0.82 (t, 3H, J = 7.2 Hz) | −0.065 |
| 4 | (+)-1-{[2-(methoxymethyl)-6-(trifluoromethyl)imidazo[2,1-b][1,3,4]thiadiazol-5-yl]methyl}-4-propylimidazolidin-2-one | 378 | 6.76 (s, 1H), 4.84 (s, 2H), 4.62 (dd, 3H, J = 69.8, 15.5 Hz), 3.44 (s, 4H), 3.35 (m, 1H), 2.81 (t, 1H, J = 7.7 Hz), 1.27 (m, 5H), 0.82 (t, 4H, J = 7.2 Hz) | +0.075 |
| 5 | 1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one | 432 | 6.87 (s, 1H), 4.86 (m, 2H), 4.64 (s, 2H), 3.54 (d, 1H, J = 6.6 Hz), 3.44 (s, 4H), 3.38 (m, 1H), 3.31 (s), 2.93 (m, 1H), 2.25 (m, 2H), 1.58 (m, 2H) | |
| 6 | (−)-1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one | 432 | 6.86 (s, 1H), 4.83 (m, 2H), 4.63 (m, 2H), 3.54 (m, 1H), 3.44 (s, 3H), 3.37 (t, 1H, J = 8.6 Hz), 2.92 (dd, 1H, J = 8.5, 6.2 Hz), 2.25 (m, 2H), 1.57 (m, 2H) | |

TABLE I-continued

Physical Characterization of Example Compounds.

| n° | IUPAC NAME | MN+ | 1H NMR δ (DMSO) | alpha_D |
|---|---|---|---|---|
| 7 | (+)-1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one | 432 | 6.86 (s, 1H), 4.83 (dd, 2H, J = 16.5, 14.3 Hz), 4.63 (m, 2H), 3.55 (m, 1H), 3.44 (s, 3H), 3.37 (t, 2H, J = 8.6 Hz), 2.92 (dd, 1H, J = 8.5, 6.2 Hz), 2.23 (m, 2H), 1.57 (m, 2H) | +0.071 |
| 8 | 1-{[6-chloro-2-(methoxymethyl)imidazo[2,1-b][1,3,4]thiadiazol-5-yl]methyl}-4-(3,3,3-trifluoropropyl)imidazolidin-2-one | 398/400 | — | |
| 9 | (−)-1-{[6-chloro-2-(methoxymethyl)imidazo[2,1-b][1,3,4]thiadiazol-5-yl]methyl}-4-(3,3,3-trifluoropropyl)imidazolidin-2-one | 398/400 | 6.84 (s, 1H), 4.82 (dd, 2H, J = 15.7, 14.3 Hz), 4.50 (dd, 2H, J = 29.5, 15.6 Hz), 3.56 (m, 1H), 3.42 (s, 3H), 3.38 (m, 1H), 2.94 (dd, 1H, J = 8.5, 6.4 Hz), 2.25 (m, 2H), 1.58 (m, 2H) | −0.153 |
| 10 | (+)-1-{[6-chloro-2-(methoxymethyl)imidazo[2,1-b][1,3,4]thiadiazol-5-yl]methyl}-4-(3,3,3-trifluoropropyl)imidazolidin-2-one | 398/400 | 6.84 (s, 1H), 4.82 (dd, 2H, J = 15.9, 14.1 Hz), 4.50 (dd, 2H, J = 29.5, 15.6 Hz), 3.56 (m, 1H), 3.42 (s, 3H), 3.38 (m, 1H), 2.93 (dd, 1H, J = 8.6, 6.3 Hz), 2.24 (m, 2H), 1.59 (m, 2H) | +0.125 |
| 11 | 1-{[2-(methoxymethyl)-6-(trifluoromethyl)imidazo[2,1-b][1,3,4]thiadiazol-5-yl]methyl}-4-(2,2,2-trifluoroethyl)imidazolidin-2-one | 418 | 6.80 (s, 1H), 4.84 (s, 2H), 4.65 (dd, 2H), 3.78 (t, 1H, J = 6.7 Hz), 3.48 (m, 1H), 3.44 (s, 3H), 3.05 (t, 1H, J = 7.8 Hz), 2.38 (m, 1H) | |
| 12 | 4-(2-chloro-2,2-difluoroethyl)-1-{[2-(methoxymethyl)-6-(trifluoromethyl)imidazo[2,1-b][1,3,4]thiadiazol-5-yl]methyl}imidazolidin-2-one | 434/436 | — | |
| 13 | (+)-4-(2-chloro-2,2-difluoroethyl)-1-{[2-(methoxymethyl)-6-(trifluoromethyl)imidazo[2,1-b][1,3,4]thiadiazol-5-yl]methyl}imidazolidin-2-one | 434/436 | 6.80 (s, 1H), 4.85 (s, 2H), 4.66 (m, 2H), 3.83 (t, 1H, J = 6.8 Hz), 3.50 (t, 1H, J = 8.6 Hz), 3.45 (s, 3H), 3.10 (t, 1H, J = 7.8 Hz), 2.68 (m, 2H) | +0.032 |
| 14 | (−)-4-(2-chloro-2,2-difluoroethyl)-1-{[2-(methoxymethyl)-6-(trifluoromethyl)imidazo[2,1-b][1,3,4]thiadiazol-5-yl]methyl}imidazolidin-2-one | 434/436 | 6.80 (s, 1H), 4.85 (s, 2H), 4.66 (m, 2H), 3.84 (m, 1H), 3.50 (t, 1H, J = 8.6 Hz), 3.45 (s, 3H), 3.10 (t, 1H, J = 7.8 Hz), 2.68 (m, 2H) | −0.027 |
| 15 | (+)-1-{[2-(methoxymethyl)-6-(trifluoromethyl)-imidazo[2,1-b][1,3,4]thiadiazol-5-yl]methyl}-4-(2,2,2-trifluoroethyl)imidazolidin-2-one | 418 | 6.81 (s, 1H), 4.84 (s, 2H), 4.65 (dd, 2H), 3.78 (t, 1H, J = 6.6 Hz), 3.48 (m, 1H), 3.44 (s, 3H), 3.05 (t, 1H, J = 7.8 Hz), 2.38 (m, 2H) | +0.041 |
| 16 | (−)-1-{[2-(methoxymethyl)-6-(trifluoromethyl)-imidazo[2,1-b][1,3,4]thiadiazol-5-yl]methyl}-4-(2,2,2-trifluoroethyl)imidazolidin-2-one | 418 | 6.81 (s, 1H), 4.84 (s, 2H), 4.65 (dd, 2H), 3.78 (t, 1H, J = 6.7 Hz), 3.48 (m, 1H), 3.44 (s, 3H), 3.05 (t, 1H, J = 7.8 Hz), 2.38 (m, 2H) | |
| 17 | 4-(2,2-difluoroethenyl)-1-{[2-(methoxymethyl)-6-(trifluoromethyl)imidazo[2,1-b][1,3,4]thiadiazol-5-yl]methyl}imidazolidin-2-one | 398 | — | |
| 18 | 4-(2-chloro-2,2-difluoroethyl)-1-{[2-(hydroxymethyl)-6-(trifluoromethyl)imidazo[2,1-b][1,3,4]thiadiazol-5-yl]methyl}imidazolidin-2-one | 420/422 | 6.79 (s, 1H), 6.53 (dd, J = 5.5 Hz, 1H), 4.84 (d, J = 5.1 Hz, 2H), 4.63 (m, 2H), 3.83 (m, 1H), 3.47 (dd, 1H, J = 8.6 Hz), 3.07 (m, 1H), 2.67 (m, 2H) | |
| 19 | 1-{[2-(hydroxymethyl)-6-(trifluoromethyl)imidazo[2,1-b][1,3,4]thiadiazol-5-yl]methyl}-4-(2,2,2-trifluoroethyl)imidazolidin-2-one | 404 | 6.81 (s, 1H), 6.53 (s, 1H), 4.84 (d, J = 3.5 Hz, 2H), 4.63 (m, 2H), 3.78 (m, 1H), 3.45 (dd, 1H, J = 8.6 Hz), 3.04 (dd, J = 7.9 Hz, 1H), 2.39 (m, 2H) | |
| 20 | (−)-1-{[2-(methoxymethyl)-6-(trifluoromethyl)imidazo[2,1-b][1,3,4]thiadiazol-5-yl]methyl}-4-(2-methylpropyl)imidazolidin-2-one | 392 | 6.76 (s, 1H), 4.84 (s, 2H), 4.62 (dd, 2H), 3.52 (quint, 1H, J = 7.1 Hz), 3.44 (s, 3H), 3.38 (m, 1H), 3.31 (s, 1H), 2.80 (t, 1H, J = 7.7 Hz), 1.58 (m, 1H), 1.32 (m, 1H), 1.17 (m, 1H), 0.82 (t, 6H, J = 6.1 Hz) | −0.135 |
| 21 | (+)-1-{[2-(methoxymethyl)-6-(trifluoromethyl)imidazo[2,1-b][1,3,4]thiadiazol-5-yl]methyl}-4- | 392 | 6.76 (s, 1H), 4.84 (s, 2H), 4.62 (dd, 2H), 3.52 (quint, 1H, J = 7.1 Hz), 3.44 (s, 3H), 3.37 (m, 1H), | +0.151 |

TABLE I-continued

Physical Characterization of Example Compounds.

| n° | IUPAC NAME | MN+ | $^1$H NMR δ (DMSO) | alpha$_D$ |
|---|---|---|---|---|
|  | (2-methylpropyl)imidazolidin-2-one |  | 3.31 (s, 1H), 2.80 (t, 1H, J = 7.7 Hz), 1.58 (m, 1H), 1.32 (m, 1H), 1.18 (m, 1H), 0.81 (t, 6H, J = 6.1 Hz) |  |
| 22 | (+)-4-(2-chloro-2,2-difluoroethyl)-1-{[2-(methoxymethyl)-6-(trifluoromethyl)imidazo[2,1-b][1,3,4]thiadiazol-5-yl]methyl}-3-methylimidazolidin-2-one | 448/ 450 | 4.83 (s, 2H), 4.68 (dd, 2H), 3.65 (m, 1H), 3.49 (t, J = 8.6 Hz, 1H), 3.43 (s, 3H), 3.13 (t, J = 8.1 Hz, 1H), 3.02 (qd, J = 15.6, 2.5 Hz, 1H), 2.67 (m, 4H). | +0.180 |
| 23 | (−)-4-(2-chloro-2,2-difluoroethyl)-1-{[2-(methoxymethyl)-6-(trifluoromethyl)imidazo[2,1-b][1,3,4]thiadiazol-5-yl]methyl}-3-methylimidazolidin-2-one | 448/ 450 | 4.83 (s, 2H), 4.68 (dd, 2H), 3.65 (m, 1H), 3.48 (t, J = 8.6 Hz, 1H), 3.43 (s, 3H), 3.12 (t, J = 8.1 Hz, 1H), 3.03 (qd, J = 15.6, 2.4 Hz, 1H), 2.67 (m, 4H). |  |

Example 6

Binding Assay to SV2A

The inhibition constant (Ki) of a compound is determined in competitive binding experiments by measuring the binding of a single concentration of a radioactive ligand at equilibrium with various concentrations of the unlabeled test substance. The concentration of the test substance inhibiting 50% of the specific binding of the radioligand is called the $IC_{50}$. The equilibrium dissociation constant Ki is proportional to the $IC_{50}$ and is calculated using the equation of Cheng and Prusoff (Cheng Y. et al., Biochem. Pharmacol. (1972), 22, 3099-3108).

The concentration range usually encompasses 6 log units with variable steps (0.3 to 0.5 log). Assays are performed in mono- or duplicate, each Ki determination is performed on two different samples of test substance.

Cerebral cortex from 200-250 g male Sprague-Dawley rats are homogenised using a Potter S homogeniser (10 strokes at 1,000 rpm; Braun, Germany) in 20 mmol/l Tris-HCl (pH 7.4), 250 mmol/l sucrose (buffer A); all operations are performed at 4° C. The homogenate is centrifuged at 30,000 g for 15 min. The crude membrane pellet obtained is resuspended in 50 mmol/l Tris-HCl (pH 7.4), (buffer B) and incubated 15 min at 37° C., centrifuged at 30,000 g for 15 min and washed twice with the same buffer. The final pellet is resuspended in buffer A at a protein concentration ranging from 15 to 25 mg/ml and stored in liquid nitrogen.

Membranes (150-200 μg of protein/assay) are incubated at 4° C. for 120 min in 0.5 ml of a 50 mmol/l Tris-HCl buffer (pH 7.4) containing 2 mmol/l $MgCl_2$, 1 to 2 $10^{-9}$ mol/l of [3H]-2-[4-(3-azidophenyl)-2-oxo-1-pyrrolidinyl]butanamide and increasing concentrations of the test compound of formula I. The non specific binding (NSB) is defined as the residual binding observed in the presence of a concentration of reference substance (e.g. $10^{-3}$ mol/l levetiracetam) that binds essentially all the receptors. Membrane-bound and free radioligands are separated by rapid filtration through glass fiber filters (equivalent to Whatman GF/C or GF/B; VEL, Belgium) pre-soaked in 0.1% polyethyleneimine and $10^{-3}$ mol/l levetiracetam to reduce non specific binding. Samples and filters are rinsed by at least 6 ml of 50 mmol/l Tris-HCl (pH 7.4) buffer. The entire filtration procedure does not exceed 10 seconds per sample. The radioactivity trapped onto the filters is counted by liquid scintillation in a p-counter (Tri-Carb 1900 or TopCount 9206, Camberra Packard, Belgium, or any other equivalent counter). Data analysis is performed by a computerized non linear curve fitting method using a set of equations describing several binding models assuming populations of independent non-interacting receptors, which obey the law of mass.

Compounds of formula (I) according to the invention typically show $pIC_{50}$ values of at least about 7.0.

Example 7

Binding Assay to SV2C

For this assay, SV2C expressed in COS-7 cells are used under standard conditions. [$^3$H]-(+)-4-(3-azido-2,4-difluorophenyl)-1-(1H-imidazol-1-ylmethyl) pyrrolidin-2-one is the used as the radio ligand that binds selectively to SV2C whereby the differential binding of the test compounds is measured, the $IC_{50}$s of the test compounds are calculated under conditions known to a person skilled in the art.

Compounds of formula (I) according to the invention typically show $pIC_{50}$ values of at least 6.0.

Example 8

Seizure Models

The following 3 seizure models are viewed to be predictive in the assessment of compounds that are potentially useful in the control of seizures in patients with epilepsy. In addition, the 6 Hz seizure model has been proposed to be useful for identification of compounds possessing clinical activity in patients with refractory seizures (Barton et al., Epilepsy Res. (2001), 47, 217-27).

8.1 Animal model of sound-susceptible mice (audiogenic seizures).

The objective of this test is to evaluate the anticonvulsant potency of a compound in sound-susceptible mice, a genetic animal model with reflex seizures. In this model of primary generalised epilepsy, seizures are evoked without electrical or chemical stimulation and the seizure types are, at least in part, similar in their clinical phenomenology to seizures occurring in man (Löscher W. & Schmidt D., Epilepsy Res. (1998), 2, 145-181; Buchhalter J. R., Epilepsia (1993), 34, S31-S41).

Male or female genetically sound-sensitive mice (14-28 g; N=10), derived from a DBA strain originally selected by Dr. Lehmann of the Laboratory of Acoustic Physiology (Paris) and bred in the UCB Pharma Sector husbandry unit since 1978, are used. The experimental design consisted of several groups, one group receiving the vehicle control and the other groups different doses of the test-compound. The compounds are administered intraperitoneally 60 minutes before the induction of audiogenic seizures. The range of the doses administered had a logarithmic progression, generally between 1.0×10-5 mol/kg and 1.0×10-3 mol/kg, but lower or higher doses are tested if necessary.

For testing, the animals are placed in small cages, one mouse per cage, in a sound-attenuated chamber. After a period of orientation of 30 seconds, the acoustic stimulus (90 dB, 10-20 kHz) is delivered for 30 seconds via loudspeakers positioned above each cage. During this interval, the mice are observed and the presence of the 3 phases of the seizure activity namely wild running, clonic and tonic convulsions, is recorded. The proportion of mice protected against wild running, clonic and tonic convulsions, respectively, is calculated.

For active compounds, an ED50 value, i.e. the dose producing 50% protection relative to the control group, together with 95% confidence limits, is calculated using a Probit Analysis (SAS/STAT® Software, version 6.09, PROBIT procedure) of the proportions of protected mice for each of the 3 phases of the seizure activity.

Compounds synthesized according to the procedure described in examples 1 to 3 and described in table 1 are tested in the audiogenic seizure in mice, according to the procedure described above, and are found active.

8.2 6 Hz Seizure Model

Male NMRI mice (Charles River, France) weighing 20-30 g are used in all experiments. The animals are kept on a 12/12-h light/dark cycle with lights on at 0600 h and are housed at a temperature maintained at 20-21° C. and at humidity of about 40%. The mice are housed in groups of 10 per cage (38×26×14 cm). All animals have free access to standard pellet food and water before random assignment to experimental groups consisting of 10 mice each. All animal experiments are done according to the Helsinki declaration and conducted in accordance with the guidelines of the European Community Council directive 86/609/EEC. A local ethical committee approved the experimental protocol.

The 6 Hz model is carried out according to a previously described protocol (Kaminski et al., Epilepsia (2004), 45, 864-867). Briefly, corneal stimulation (44 mA, 0.2 ms-duration monopolar rectangular pulses at 6 Hz for 3 s) is delivered by a constant-current device (ECT Unit 57800; Ugo Basile, Comerio, Italy). A drop of 0.4% oxybuprocaine hydrochloride (Unicaine, Thea, France) is placed on the eyes before electrical stimulation. During the stimulation, mice are manually restrained and released into the observation cage (38× 26×14 cm) immediately after the current application. The seizures are often preceded by a brief period (~2-3 s) of intense locomotor agitation (wild running and jumping). The animals then exhibit a "stunned" posture associated with rearing, forelimb automatic movements and clonus, twitching of the vibrissae, and Strub-tail. At the end of the seizure, animals resume their normal exploratory behavior. The experimental endpoint is protection against the seizure. The animal is considered to be protected if it resumes its normal exploratory behavior within 7 s from the stimulation.

In vivo activities determined for test compounds are typically comprised between 0.05 mg/kg and 10 mg/kg.

8.3 Pentylenetetrazol (PTZ) Seizure Model

Animals are prepared as described in example 6.2.

Pentylenetetrazol is used at the previously established CD97 dose of 89 mg/kg; a convulsive dose inducing clonic convulsions of all four extremities in 97% of mice (Klitgaard et al., Eur. J. Pharmacol. (1998), 353, 191-206). Immediately following pentylenetetrazol injection the mice are placed individually in Perspex cages and observed for the presence of clonic convulsions in all four extremities and tonic hindlimb extension during 60 min period.

The invention claimed is:

1. A compound of formula (I), a geometrical isomer, an enantiomer, a diastereomer, or mixtures thereof, or a pharmaceutically acceptable salt thereof,

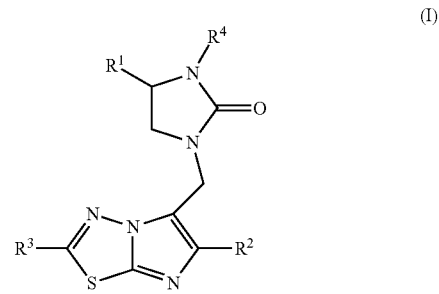

(I)

wherein
$R^1$ is a $C_{1-4}$ alkyl or a $C_{2-4}$ alkenyl optionally substituted by one or more halogen substituents;
$R^2$ is either a halogen or a $C_{1-4}$ alkyl containing at least one halogen substituent;
$R^3$ is a $C_{1-4}$ alkyl containing at least one hydroxy or an alkoxy substituent;
$R^4$ is either hydrogen or a methyl group.

2. A compound of formula (I-A) according to claim 1, wherein

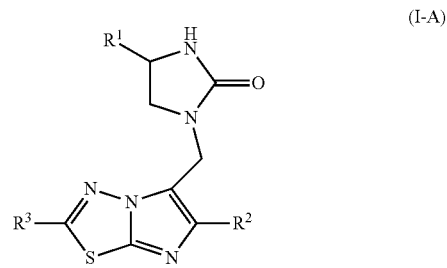

(I-A)

wherein
$R^1$ is a $C_{1-4}$ alkyl optionally substituted by one or more halogen substituents;
$R^2$ is either a halogen or a $C_{1-4}$ alkyl containing at least one halogen substituent;
$R^3$ is a $C_{1-4}$ alkyl containing at least one hydroxy or an alkoxy substituent.

3. A compound of formula (IB) according to claim 1, wherein

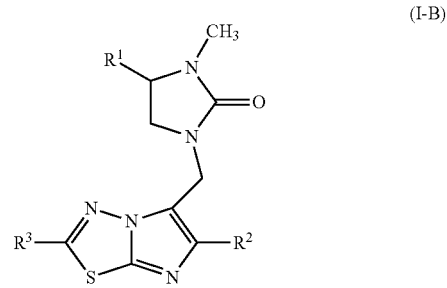

(I-B)

wherein
R¹ is a $C_{1-4}$ alkyl or a $C_{2-4}$ alkenyl optionally substituted by one or more halogen substituents;
R² is either a halogen or a $C_{1-4}$ alkyl containing at least one halogen substituent;
R³ is a $C_{1-4}$ alkyl containing at least one hydroxy (OH) or an alkoxy substituent.

4. A compound according to claim 1, wherein R¹ is an i-butyl, n-propyl, 2,2-difluoropropyl, a 2-chloro-2,2-difluoroethyl, a 2,2-difluoroethyl, a 2,2,2-trifluoroethyl, a 3,3,3-trifluoropropyl, a 2-fluoroethyl or a 2,2-difluoroethenyl moiety.

5. A compound according to claim 1, wherein R¹ is an i-butyl, n-propyl, 2,2-difluoropropyl, a 2-chloro-2,2-difluoroethyl, a 2,2-difluoroethyl, a 2,2,2-trifluoroethyl, a 3,3,3-trifluoropropyl or a 2-fluoroethyl moiety.

6. A compound according to claim 1, wherein R² is a chloro, a difluoromethyl or a trifluoromethyl moiety.

7. A compound according to claim 1, wherein R³ is either a hydroxymethyl, a methoxymethyl, a [($^2H_3$)methyloxy]methyl, a methoxy($^2H_2$) methyl, a (2,2,2-trifluoroethoxy)methyl or a 2-methoxyethyl moiety.

8. A compound according to claim 1, wherein
R¹ is a i-butyl, n-propyl, a 2-chloro-2,2-difluoroethyl, a 2,2,2-trifluoroethyl or a 3,3,3-trifluoropropyl moiety;
R² is a chloro or a trifluoromethyl moiety;
R³ is a methoxymethyl moiety.

9. A compound according to claim 1 selected from the group consisting of:
1-{[2-(methoxymethyl)-6-(trifluoromethyl)imidazo[2,1-b][1,3,4]thiadiazol-5-yl]methyl}-4-(2-methylpropyl)imidazolidin-2-one;
(−)-1-{[2-(methoxymethyl)-6-(trifluoromethyl)imidazo[2,1-b][1,3,4]thiadiazol-5-yl]methyl}-4-(2-methylpropyl)imidazolidin-2-one;
(+)-1-{[2-(methoxymethyl)-6-(trifluoromethyl)imidazo[2,1-b][1,3,4]thiadiazol-5-yl]methyl}-4-(2-methylpropyl)imidazolidin-2-one;
1-{[2-(methoxymethyl)-6-(trifluoromethyl)imidazo[2,1-b][1,3,4]thiadiazol-5-yl]methyl}-4-propylimidazolidin-2-one;
(−)-1-{[2-(methoxymethyl)-6-(trifluoromethyl)imidazo[2,1-b][1,3,4]thiadiazol-5-yl]methyl}-4-propylimidazolidin-2-one;
(+)-1-{[2-(methoxymethyl)-6-(trifluoromethyl)imidazo[2,1-b][1,3,4]thiadiazol-5-yl]methyl}-4-propylimidazolidin-2-one;
1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one;
(−)-1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one;
(+)-1-{[2-(methoxymethyl)-6-(trifluoromethyl)imidazo[2,1-b][1,3,4]thiadiazol-5-yl]methyl}-4-(3,3,3-trifluoropropyl)imidazolidin-2-one;
1-{[6-chloro-2-(methoxymethyl)imidazo[2,1-b][1,3,4]thiadiazol-5-yl]methyl}-4-(3,3,3-trifluoropropyl)imidazolidin-2-one;
(−)-1-{[6-chloro-2-(methoxymethyl)imidazo[2,1-b][1,3,4]thiadiazol-5-yl]methyl}-4-(3,3,3-trifluoropropyl)imidazolidin-2-one;
(+)-1-{[6-chloro-2-(methoxymethyl)imidazo[2,1-b][1,3,4]thiadiazol-5-yl]methyl}-4-(3,3,3-trifluoropropyl)imidazolidin-2-one;
1-{[2-(methoxymethyl)-6-(trifluoromethyl)imidazo[2,1-b][1,3,4]thiadiazol-5-yl]methyl}-4-(2,2,2-trifluoroethyl)imidazolidin-2-one;
(+)-1-{[2-(methoxymethyl)-6-(trifluoromethyl)imidazo[2,1-b][1,3,4]thiadiazol-5-yl]methyl}-4-(2,2,2-trifluoroethyl)imidazolidin-2-one;
(−)-1-{[2-(methoxymethyl)-6-(trifluoromethyl)imidazo[2,1-b][1,3,4]thiadiazol-5-yl]methyl}-4-(2,2,2-trifluoroethyl)imidazolidin-2-one;
4-(2-chloro-2,2-difluoroethyl)-1-{[2-(methoxymethyl)-6-(trifluoromethyl)-imidazo[2,1-b][1,3,4]thiadiazol-5-yl]methyl}imidazolidin-2-one;
(+)-4-(2-chloro-2,2-difluoroethyl)-1-{[2-(methoxymethyl)-6-(trifluoromethyl)imidazo[2,1-b][1,3,4]thiadiazol-5-yl]methyl}imidazolidin-2-one;
(−)-4-(2-chloro-2,2-difluoroethyl)-1-{[2-(methoxymethyl)-6-(trifluoro-methyl)imidazo[2,1-b][1,3,4]thiadiazol-5-yl]methyl}imidazolidin-2-one;
4-(2,2-difluoroethenyl)-1-{[2-(methoxymethyl)-6-(trifluoromethyl)imidazo[2,1-b][1,3,4]thiadiazol-5-yl]methyl}imidazolidin-2-one;
4-(2-chloro-2,2-difluoroethyl)-1-{[2-(hydroxymethyl)-6-(trifluoromethyl)-imidazo[2,1-b][1,3,4]thiadiazol-5-yl]methyl}imidazolidin-2-one;
1-{[2-(hydroxymethyl)-6-(trifluoromethyl)imidazo[2,1-b][1,3,4]thiadiazol-5-yl]methyl}-4-(2,2,2-trifluoroethyl)imidazolidin-2-one;
(+)-4-(2-chloro-2,2-difluoroethyl)-1-{[2-(methoxymethyl)-6-(trifluoromethyl)-imidazo[2,1-b][1,3,4]thiadiazol-5-yl]methyl}-3-methylimidazolidin-2-one; and
(−)-4-(2-chloro-2,2-difluoroethyl)-1-{[2-(methoxymethyl)-6-(trifluoromethyl)-imidazo[2,1-b][1,3,4]thiadiazol-5-yl]methyl}-3-methylimidazolidin-2-one.

10. A pharmaceutical composition comprising an effective amount of a compound according to claim 1 in combination with a pharmaceutically acceptable diluent or carrier.

* * * * *